(12) United States Patent  
Sun

(10) Patent No.: US 9,951,085 B2
(45) Date of Patent: Apr. 24, 2018

(54) LABELED CHEMICALLY REACTIVE AND BIOLOGICALLY ACTIVE COMJUGATES, AND METHODS AND COMPOSITIONS THEREOF

(71) Applicant: Yi Sun, Wellesley, MA (US)

(72) Inventor: Yi Sun, Wellesley, MA (US)

(*) Notice: Subject to any disclaimer, the term of this patent is extended or adjusted under 35 U.S.C. 154(b) by 512 days.

(21) Appl. No.: 14/307,068

(22) Filed: Jun. 17, 2014

(65) Prior Publication Data

US 2015/0361090 A1 Dec. 17, 2015

(51) Int. Cl.

| C07D 495/04 | (2006.01) |
| C07D 311/82 | (2006.01) |
| C07D 405/12 | (2006.01) |
| C07D 475/04 | (2006.01) |
| G01N 33/58 | (2006.01) |

(52) U.S. Cl.
CPC .......... C07D 495/04 (2013.01); C07D 311/82 (2013.01); C07D 405/12 (2013.01); C07D 475/04 (2013.01); G01N 33/582 (2013.01); *Y10T 436/143333* (2015.01)

(58) Field of Classification Search
CPC .. C07D 311/82; C07D 405/12; C07D 475/04; C07D 495/04; G01N 33/582; Y10T 436/143333
See application file for complete search history.

(56) References Cited

U.S. PATENT DOCUMENTS

2010/0197030 A1 * 8/2010 Mao ................. C07D 311/88 436/73
2015/0018540 A1 * 1/2015 Prakash ................ C12N 15/111 536/24.5

FOREIGN PATENT DOCUMENTS

WO WO 0204476 A2 * 1/2002 ......... C07D 207/416
WO WO 2013033230 A1 * 3/2013 ........... C12N 15/111

OTHER PUBLICATIONS

Liu et al (Molecular Imaging and Biology, published online Apr. 2010, vol. 12, pp. 595-607).*
Gruber et al (Bioconjugate Chemistry, 1997, vol. 8, pp. 552-559).*

* cited by examiner

*Primary Examiner* — Mark V Stevens
(74) *Attorney, Agent, or Firm* — Milstein Zhang & Wu LLC

(57) ABSTRACT

The invention generally relates to novel fluorophore-labeled, bi- or multi-functional, chemically reactive and/or biologically active conjugates, and related compositions and methods thereof.

6 Claims, No Drawings

LABELED CHEMICALLY REACTIVE AND BIOLOGICALLY ACTIVE COMJUGATES, AND METHODS AND COMPOSITIONS THEREOF

TECHNICAL FIELDS OF THE INVENTION

The invention generally relates to novel compounds useful for biological detection, diagnostics and therapeutics. More particularly, the invention relates to novel fluorophore-labeled, bi- or multi-functional, chemically reactive and/or biologically active conjugates, and related compositions and methods thereof.

BACKGROUND OF THE INVENTION

Recently, there has been significant interest in molecular probes as the vehicle for detection of biomarkers as tools for research in molecular biology as well as for diagnostics of various diseases and conditions. The molecular probe may be a conjugate molecule of an interrogatory component for interaction with the analyte and a detectable component, such as a fluorescent label, that allows monitoring and/or detection.

Antibody-drug conjugates (ADCs) are another emerging class of compounds generating significant interest. ADCs are typically designed as a targeted therapy, for example, for the cancers. ADCs are conjugate compounds having an antibody (e.g., a whole mAb or an antibody fragment) covalently linked to a biological active component (e.g., a cytotoxic payload or drug), often via a stable but releasable linkage.

Another strategy in improving therapeutics is PEGylation, a process of covalently attachment of polyethylene glycol (PEG) polymer chains to a molecular probe, a drug or therapeutic protein or antibody. Reported benefits of PEGylation include masking of an agent to reduce immunogenicity and antigenicity, and prolonging an agent's circulatory time by reducing renal clearance, as well as providing water solubility to hydrophobic drugs and proteins.

While these above-mentioned strategies have drawn increasing interests, a number of outstanding issues and limitations remain that affect the scope and effectiveness in actual applications. Novel approaches are desired that afford novel compounds, compositions and methodologies with expanded functionalities and utilities.

SUMMARY OF THE INVENTION

The invention provides novel fluorophore-labeled, bi- or multi-functional, chemically reactive and/or biologically active conjugates, and related compositions and methods thereof. The conjugate compounds and methods disclosed herein are technical fields of ADCs, PEGylation and molecular diagnostics, for example, as building blocks, precursors and/or molecular probes or drug conjugates.

In one aspect, the invention generally relates to a compound having the formula I:

  (I)

wherein P is a linear or branched oligomer comprising from 1 to about 2,000 ethylene oxide units; A is selected from $X_m$-$L^1$ and (X-$L^1$)$_m$; and B is selected from $L^2$-$Y_n$ and ($L^2$-Y)$_n$. Each of $L^1$ and $L^2$ independently is a bond or linker. At each occurrence, X independently is a fluorescently detectable moiety. At each occurrence, Y independently is a chemically reactive or biologically active moiety. n is an integer from 1 to about 10. n is an integer from 1 to about 10.

In certain embodiments, the compound has formula II:

  (II)

wherein P is a linear or branched oligomer comprising from 1 to about 2,000 ethylene oxide units. Each of $L^1$ and $L^2$ independently is a bond or linker. X, at each occurrence, independently is fluorescently detectable moiety. Y, at each occurrence, independently is a chemically reactive or biologically active moiety. m is an integer from 1 to about 10, and n is an integer from 1 to about 10.

In certain embodiments, the compound has formula III:

  (III)

wherein P is a linear or branched oligomer comprising from 1 to about 2,000 ethylene oxide units. Each of $L^1$ and $L^2$ independently is a bond or linker. X, at each occurrence, independently is fluorescently detectable moiety. Y, at each occurrence, independently is a chemically reactive or biologically active moiety. m is an integer from 1 to about 10, and n is an integer from 1 to about 10.

DEFINITIONS

Unless defined otherwise, all technical and scientific terms used herein have the same meaning as commonly understood by one of ordinary skill in the art to which this invention belongs.

The term "alkyl", as used herein, refers to a saturated straight chain, branched or cyclic hydrocarbon group (e.g., having 1 to 24, typically 1 to 12) carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. Alkyls include "cycloalkys", which refer to cyclic alkyl groups such as cyclopropyl, cyclobutyl, cyclopentyl, cyclohexyl, cycloheptyl and cyclooctyl.

The term "alkylene", as used herein, refers to a straight, branched chain or cyclic divalent radicals having up to 50 carbons, unless the chain length or ring size is limited thereto. Typical examples include methylene (—CH$_2$—), ethylene (—CH$_2$CH$_2$—), hexylene, heptylene, octylene, nonylene, and decylene, among others.

The term "amino", as used herein, refers to the group —NR'R" (or NRR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —NRR'R" and its biologically compatible anionic counterions.

The term "amino acid", as used herein, refers to not only the L, D- and nonchiral forms of the common naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, epsilon-nicotinoyl-lysine, isonipecotic acid, tetrahydroisoquinoleic acid, sarcosine, citrulline, cysteic acid, t-butylglycine, t-butylalanine, phenylglycine, cyclohexylalanine, beta-alanine, 4-aminobutyric acid, and the like.

The term "antibody", as used herein, refers to molecules that are capable of binding an epitope or antigenic determinant. The term is meant to include whole antibodies and antigen-binding fragments thereof, including single-chain antibodies. The antibodies can be from any animal origin. Preferably, the antibodies are mammalian, e.g., human, murine, rabbit, goat, guinea pig, camel, horse and the like, or other suitable animals. Antibodies may recognize polypeptide or polynucleotide antigens. The term includes active fragments, including for example, an antigen binding fragment of an immunoglobulin, a variable and/or constant region of a heavy chain, a variable and/or constant region of a light chain, a complementarity determining region (cdr), and a framework region. The terms include polyclonal and monoclonal antibody preparations, as well as preparations including hybrid antibodies, altered antibodies, chimeric antibodies, hybrid antibody molecules, F(ab)$_2$ and F(ab) fragments; Fv molecules (for example, noncovalent heterodimers), dimeric and trimeric antibody fragment constructs; minibodies, humanized antibody molecules, and any functional fragments obtained from such molecules, wherein such fragments retain specific binding.

The term "biologically active" entity or an entity having "biological activity," as used herein, refers to one having structural, regulatory, or biochemical functions of a naturally occurring molecule or any function related to or associated with a metabolic or physiological process. Biologically active polynucleotide fragments are those exhibiting activity similar, but not necessarily identical, to an activity of a polynucleotide of the present invention. The biological activity can include an improved desired activity, or a decreased undesirable activity. For example, an entity demonstrates biological activity when it participates in a molecular interaction with another molecule, such as hybridization, when it has therapeutic value in alleviating a disease condition, when it has prophylactic value in inducing an immune response, when it has diagnostic and/or prognostic value in determining the presence of a molecule, such as a biologically active fragment of a polynucleotide that can, for example, be detected as unique for the polynucleotide molecule, or that can be used as a primer in a polymerase chain reaction. A biologically active polypeptide or fragment thereof includes one that can participate in a biological reaction.

The term "biomolecule" may refer to a compound found in nature, a derivative of a compound found in nature, a synthetically modified analog of a compound found in nature, a genetically engineered analog of a compound found in nature, a genetically engineered modified analog of a compound found in nature. For example, biomolecules may be and/or include proteins; antibodies; antibody-fragments; haptens; glycoproteins; cell-membrane proteins; enzymes, such as alkaline phosphatase, beta-galactosidase, horseradish peroxidase, or urease; peptides; peptide nucleic acids (PNAs); locked nucleic acids (LNAs); genetically engineered peptides; genetically engineered proteins; genetically engineered antibodies; genetically engineered antibody-fragments; oligonucleotides; RNA; DNA; saccharide-containing molecules; monosaccharides; disaccharides; trisaccharides; oligosaccharides; polysaccharides, such as dextran; small molecules, including drug-like molecules; drugs; antigens, such as tumor antigens; pathogens; toxins; polymers, including biopolymers and/or dendrimers; nuclear receptors; nuclear receptor substrates and/or ligands; cytokines; epitopes, including peptide epitopes, antigen epitopes, and/or pathogen epitopes; enzyme substrates; and/or combinations or derivatives thereof.

The terms "covalent" or "covalently", as used herein, refer to the nature of a chemical bonding interaction between atoms. A covalent bond is a chemical bonding that involves the sharing of electron pairs between atoms. The stable balance of attractive and repulsive forces between atoms when they share electrons is referred to as covalent bonding. The sharing of electrons allows each atom to attain the equivalent of a full outer shell, corresponding to a stable electronic configuration. Covalent bonding includes various kinds of interactions, e.g., σ-bonding, π-bonding, metal-to-metal bonding, agostic interactions, and three-center two-electron bonds.

The terms "deoxyribonucleic acid" and "DNA", as used herein, refers to a nucleic acid composed of nucleotides deoxyribonucleotides.

The term "dye," as used herein, generally refers to any organic or inorganic molecule or moiety that absorbs electromagnetic radiation, for example, at a wavelength greater than or equal 340 nm.

The term "ethylene-oxide unit", as used herein, refers to a unit of —CH$_2$CH$_2$O—.

The term "fluorescent dye," as used herein, generally refers to any dye that emits electromagnetic radiation of longer wavelength by a fluorescent mechanism upon irradiation by a source of electromagnetic radiation, such as a lamp, a photodiode, or a laser.

The term "fluorescent label", as used herein, refers to any label detectable via fluorescent emission of the label, for example, via fluorescent spectroscopy. A biomolecule such as a nucleic acid can be directly or indirectly labeled. A nucleic acid that is directly labeled is linked to the label covalently or non-covalently.

The term "humanized" antibodies, as used herein, refer to a molecule having an antigen binding site that is substantially derived from an immunoglobulin from a non-human species and the remaining immunoglobulin structure of the molecule based upon the structure and/or sequence of a human immunoglobulin. The antigen binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Some forms of humanized antibodies preserve all CDR sequences (e.g., a humanized mouse antibody which contains all six CDRs from the mouse antibodies). Other forms of humanized antibodies have one or more CDRs (one, two, three, four, five, six) that are altered with respect to the original antibody.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

The term "label", as used herein, refers to any detectable label, including a radioactive label and a non-radioactive label. Non-radioactive labels include optically detectable labels, including fluorescent labels and fluorescent barcodes, as well as mass tagged labels. Labels include directly detectable and indirectly detectable non-radioactive labels such as fluorescent labels and mass tags.

The term "ligand", as used herein, refers to a moiety that is capable of covalently or otherwise chemically binding a compound of interest.

The term "linker", as used herein, refers to a linking moiety that connects two groups and has a backbone of 20 atoms or less in length. A linker or linkage may be a covalent bond that connects two groups or a chain of between 1 and 20 atoms in length, for example of about 1, 2, 3, 4, 5, 6, 8, 10, 12, 14, 16, 18 or 20 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, oligo(ethylene glycol); ethers, thioethers, tertiary amines, alkyls, which may be straight or branched, e.g., methyl, ethyl, n-propyl, 1-methylethyl (isopropyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

The terms "non-covalent" or "non-covalently", as used herein, refer to the nature of a chemical bonding interaction between atoms. A non-covalent bond is a type of chemical bonding that does not involve the sharing of pairs of electrons, but rather involves more dispersed variations of electromagnetic interactions. There are four commonly mentioned types of non-covalent interactions: hydrogen bonds, ionic bonds, van der Waals forces, and hydrophobic interactions.

The term "nucleic acid molecule," "nucleotide," "oligonucleotide," "polynucleotide," and "nucleic acid" are used interchangeably herein to refer to polymeric forms of nucleotides of any length, e.g., greater than about 2 bases, greater than about 10 bases, from about 10 to about 500 bases, greater than about 500 bases, greater than 1,000 bases or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleotides, e.g., can participate in Watson-Crick base pairing interactions. Naturally-occurring nucleotides include guanine, cytosine, adenine and thymine (G, C, A and T, respectively).

A nucleic acid may exist in a single stranded or a double-stranded form. A double stranded nucleic acid has two complementary strands of nucleic acid may be referred to herein as the "first" and "second" strands or some other arbitrary designation. The first and second strands are distinct molecules, and the assignment of a strand as being a first or second strand is arbitrary and does not imply any particular orientation, function or structure. The nucleotide sequences of the first strand of several exemplary mammalian chromosomal regions (e.g., BACs, assemblies, chromosomes, etc.), as well as many pathogens, are known, and may be found in NCBI's Genbank database, for example. The second strand of a region is complementary to that region.

The term "oligonucleotide", as used herein, refers to a single stranded multimer of nucleotide of from about 2 to 500 nucleotides. Oligonucleotides may be synthetic or may be made enzymatically, and, in some embodiments, are 10 to 50 nucleotides in length. Oligonucleotides may contain ribonucleotide monomers (i.e., may be oligoribonucleotides) or deoxyribonucleotide monomers. Oligonucleotides may be 10 to 20, 21 to 30, 31 to 40, 41 to 50, 51-60, 61 to 70, 71 to 80, 80 to 100, 100 to 150, 150 to 200 or greater than 200 nucleotides in length, for example.

The terms "peptide", "polypeptide" and "protein", are used interchangeably to refer to a polymer of amino acid residues, and are not limited to a minimum length. Thus, peptides, oligopeptides, dimers, multimers, and the like, are included within the definition. Both full-length proteins and fragments thereof are encompassed by the definition. The terms also include post-expression modifications of the polypeptide, for example, glycosylation, acetylation, phosphorylation, and the like. Furthermore, a "polypeptide" may refer to a protein which includes modifications, such as deletions, additions, and substitutions (generally conservative in nature), to the native sequence, as long as the protein maintains the desired activity. These modifications may be deliberate or may be accidental. The term "protein," as used herein, refers to polypeptides of specific sequence of more than about 50 residues, e.g., peptides, enzymes, glycoproteins, hormones, receptors, antigens, antibodies, growth factors, etc.

A peptide can be naturally occurring, recombinantly produced, or synthetically produced. Thus, the terms "peptide," "oligopeptide," "polypeptide" include peptides in which the conventional backbone has been replaced with non-naturally occurring or synthetic backbones, and peptides in which one or more of the conventional amino acids have been replaced with one or more non-naturally occurring or synthetic amino acids. A peptide may be made by cleavage or proteolysis (e.g., protease digestion) of a polypeptide or protein. A peptide that is produced by cleavage or proteolysis typically comprises from 2 to 50 amino acids, but other lengths are also possible.

The term "probe," as used herein, refers to a molecule or complex useful for the detection of a nucleic acid through a molecular interaction resulting in a detectable signal specifically indicating the presence of the nucleic acid analyte. A probe often possesses a nucleotide sequence that is complementary to a nucleotide sequence of interest. In certain cases, detection of a target analyte requires hybridization of a probe to a target. In certain embodiments, a probe may be immobilized on a surface of a substrate, where the substrate can have a variety of configurations, e.g., a sheet, bead, or other structure. In certain embodiments, a probe may be present on a surface of a planar support, e.g., in the form of an array.

The terms "purified" or "to purify", as used herein, refer to the removal of components (e.g., contaminants) from a sample.

The terms "ribonucleic acid" and "RNA", as used herein, refer to a nucleic acid composed of nucleotides ribonucleotides.

The term "carboxyl" refers to the group "—C(=O)OH" or "—C(=O)—O−".

The term "hydroxyl" refers to the group "—OH".

The term "thiol" refers to the group "—SH".

The term "vinyl" refers to the group "$CH_2$=CH—".

The term "vinyl sulfone" refers to the group "$CH_2$=CH—S(=O)$_2$—CH=CH)—".

The term "tosyl" refers to the group "$CH_3(C_6H_4)$S(=O)$_2$—".

Exemplary terms used herein to refer to certain reactive or functional groups are showed in the Table 1.

TABLE 1

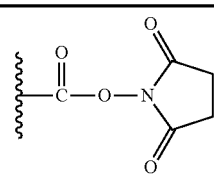

Succinimidyl ester (NHS)

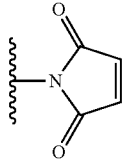 [SMILES: *N1C(=O)C=CC1=O]

Maleimide

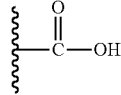

Carboxylic acid

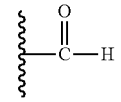 [SMILES: *C=O]

Aldehyde

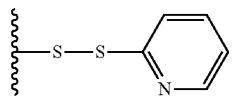

Pyridyl disulfide

TABLE 1-continued

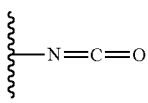 [SMILES: *N=C=O]

Isocyanate

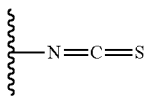

Isothiocyanate

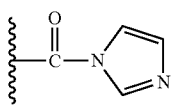

Carbonylimidazole

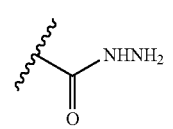

Hydrazide

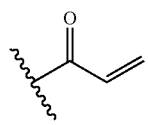

Acrylate

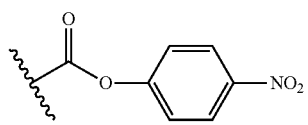 [SMILES: *C(=O)Oc1ccc([N+](=O)[O-])cc1]

Nitrophenyl carbonate

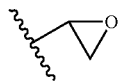

Epoxide

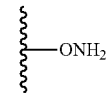

Oxyamine

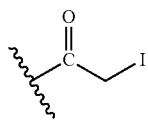

Iodoacetyl

TABLE 1-continued
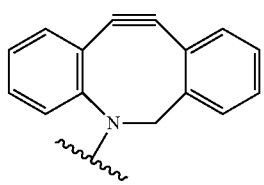 [SMILES: *N1Cc2ccccc2C#Cc2ccccc21]
Cyclooctyne
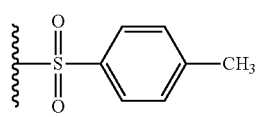 [SMILES: *S(=O)(=O)c1ccc(C)cc1]
Tosylate
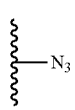
Azide
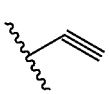
Alkyne
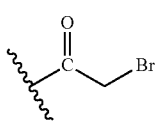 [SMILES: *C(=O)CBr]
Bromoacetyl
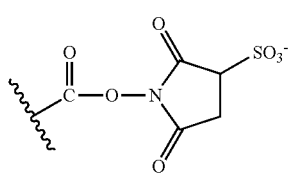
Sulfo-NHS
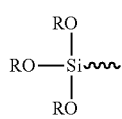
R = CH₃,
CH₃CH₂,
Alkoxyl silane
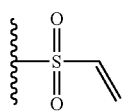
Vinyl sulfone
Exemplary terms used herein to refer to bioactive molecules or moieties are showed in Table 2.
TABLE 2
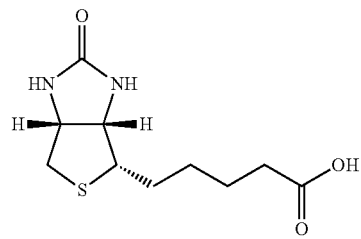 [SMILES: O=C(O)CCCC[C@@H]1SC[C@@H]2NC(=O)N[C@@H]21]
Biotin, vitamin B7
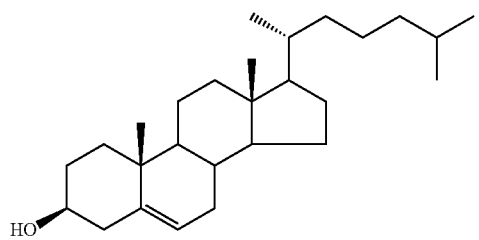 [SMILES: CC(C)CCC[C@@H](C)C1CCC2C3CC=C4C[C@@H](O)CC[C@]4(C)C3CC[C@@]21C]
Cholesterol
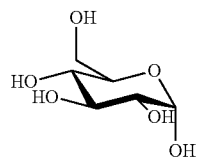
Glucose
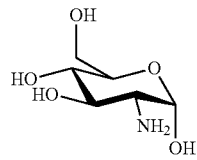
Glucosamine
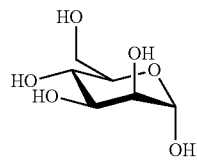
Mannose
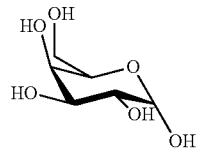
Galactose
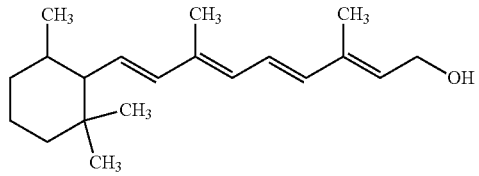 [SMILES: CC(/C=C/C1C(C)CCCC1(C)C)=C\C=C\C(C)=C\CO]
Retinol, Vitamin A TABLE 2-continued
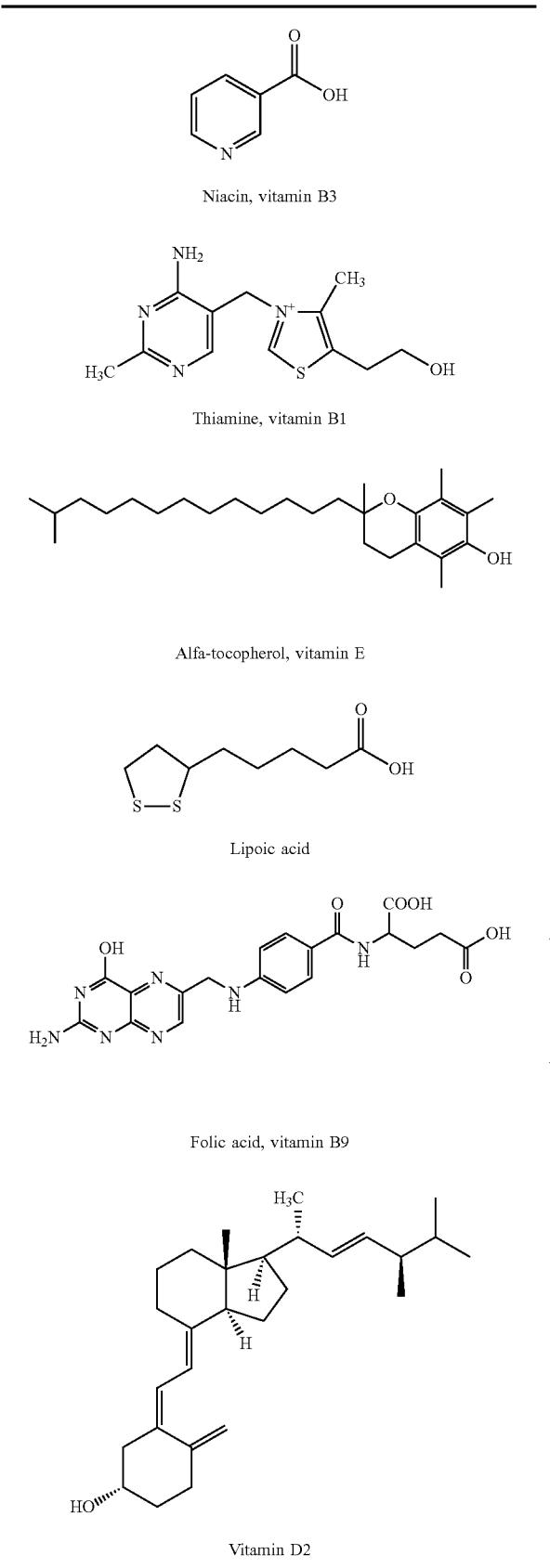
Niacin, vitamin B3
Thiamine, vitamin B1
Alfa-tocopherol, vitamin E
Lipoic acid
Folic acid, vitamin B9
Vitamin D2
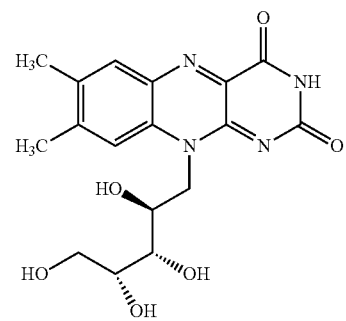 [SMILES: Cc1cc2nc3c(=O)[nH]c(=O)nc-3n(C[C@H](O)[C@H](O)[C@H](O)CO)c2cc1C]
Riboflavin, vitamin B2
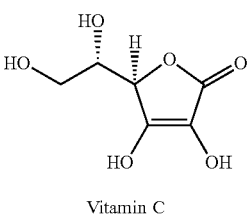
Vitamin C
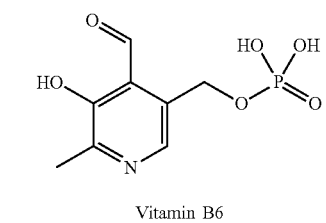
Vitamin B6
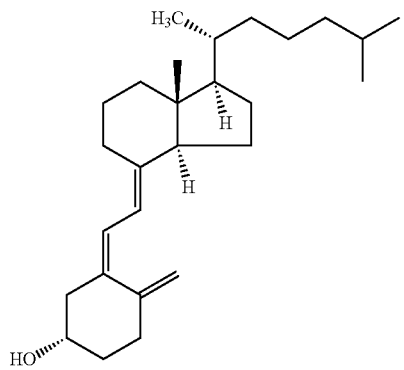
Vitamin D3
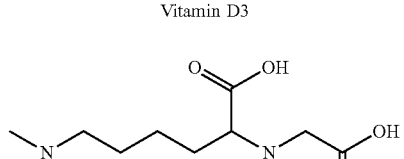
Nitrilotriacetic acid TABLE 2-continued

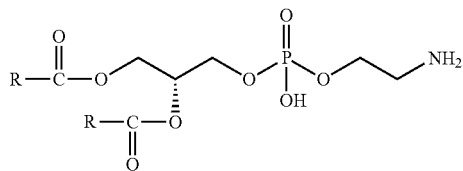

Phosphatidylethanolamine, R represents the alkyl portion of a fatty acid

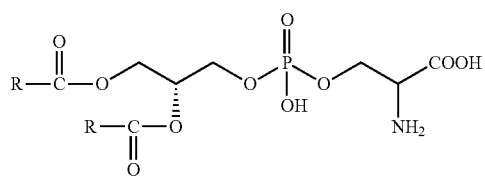

Phosphatidylserine, R represents the alkyl portion of a fatty acid

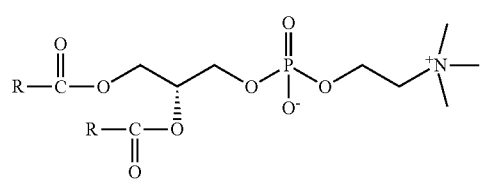

Phosphatidylcholine, R represents the alkyl portion of a fatty acid

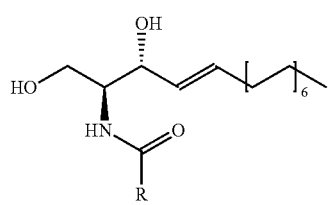

Ceramide, R represents the alkyl portion of a fatty acid.

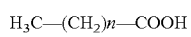

$H_3C-(CH_2)n-COOH$

Fatty acid, n from 3 to 16

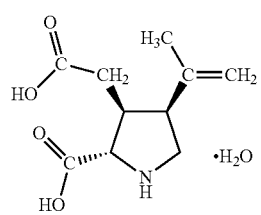

Kainic acid

TABLE 2-continued

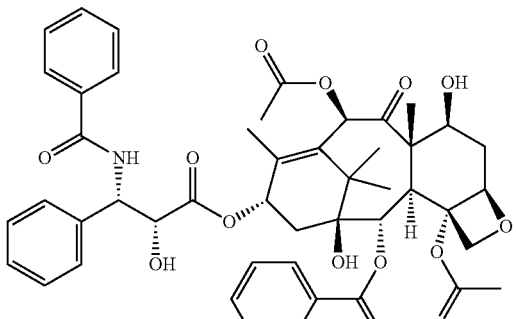

Paclitaxel

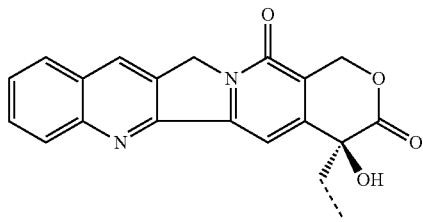

Camptothecin

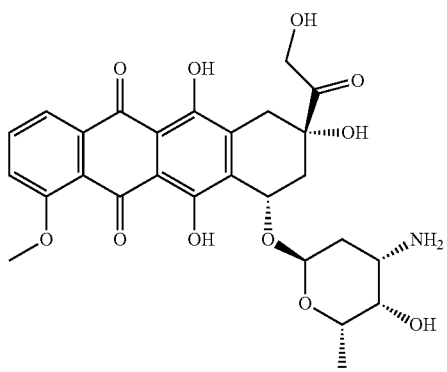 [SMILES: COc1cccc2c1C(=O)c1c(O)c3c(c(O)c1C2=O)C[C@@](O)(C(=O)CO)C[C@@H]3O[C@H]1C[C@H](N)[C@H](O)[C@H](C)O1]

Doxorubicin

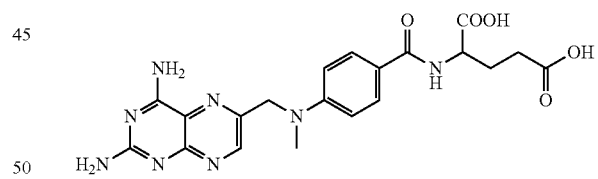

Methotrexate

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

Given the benefit of this disclosure, one of ordinary skill in the art will appreciate that synthetic methods, as described herein, may utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by preferably readily available, non-toxic reagents that do not attack the other functional groups; the protecting group forms an easily separable derivative (more preferably without the generation of new stereogenic centers); and the protecting group has a minimum of additional functionality to avoid further sites of reaction. Oxygen, sulfur, nitrogen, and carbon protecting groups may be utilized. Examples of a variety of protecting groups can be found in Protective Groups in Organic Synthesis, Third Ed. Greene, T. W. and Wuts, P. G., Eds., John Wiley & Sons, New York: 1999.

It will be appreciated that the compounds, as described herein, may be substituted with any number of substituents or functional moieties.

DESCRIPTION OF THE INVENTION

The invention provides novel conjugate compounds, compositions and methodologies with expanded functionalities and utilities in the fields of biological detection, diagnostics and therapeutics. These compounds may be utilized as building blocks, precursors and/or molecular probes or drug conjugates.

In one aspect, the invention generally relates to a compound having the formula I:

$$A\text{-}P\text{—}B \quad (I)$$

wherein P is a linear or branched oligomer comprising from 1 to about 2,000 ethylene oxide units; A is selected from $X_m\text{-}L^1$ and $(X\text{-}L^1)_m$; and B is selected from $L^2\text{-}Y_n$ and $(L^2\text{-}Y)_n$. Each of $L^1$ and $L^2$ independently is a bond or linker. At each occurrence, X independently is a fluorescently detectable moiety. At each occurrence, Y independently is a chemically reactive or biologically active moiety. n is an integer from 1 to about 10. n is an integer from 1 to about 10.

In certain embodiments, the compound has formula II:

$$X_m\text{-}L^1\text{-}P\text{-}L^2\text{-}Y_n \quad (II)$$

wherein P is a linear or branched oligomer comprising from 1 to about 2,000 ethylene oxide units. Each of $L^1$ and $L^2$ independently is a bond or linker. X, at each occurrence, independently is fluorescently detectable moiety. Y, at each occurrence, independently is a chemically reactive or biologically active moiety. m is an integer from 1 to about 10, and n is an integer from 1 to about 10.

In certain embodiments of (II), $L^1$ is

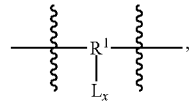

or $L^2$ is

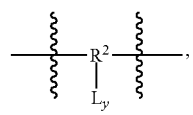

or both $L^1$ is

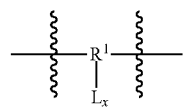

and $L^2$ is

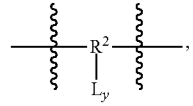

wherein each of $R^1$ and $R^2$ is independently selected from the group consisting of CR, NR, N and C(OR), wherein each R is independently H or an alkyl group (e.g., a $C_1\text{-}C_6$ alkyl); and each of $L_x$ and $L_y$ is independently a moiety selected from the group consisting of amide, ester, ether, thioether, hydrazone, urea, carbonate, thiol urea, carbamate, secondary amine bond, arylamine, amidine, phosporamidate, disulfide, sulfonamide, diazo, triazo bond formed through click chemistry.

In certain embodiments, the compound has formula III:

$$(X\text{-}L^1)_m\text{-}P\text{-}(L^2\text{-}Y)_n \quad (III)$$

wherein P is a linear or branched oligomer comprising from 1 to about 2,000 ethylene oxide units. Each of $L^1$ and $L^2$ independently is a bond or linker. X, at each occurrence, independently is fluorescently detectable moiety. Y, at each occurrence, independently is a chemically reactive or biologically active moiety. m is an integer from 1 to about 10, and n is an integer from 1 to about 10.

In certain embodiments of (III),
$L^1$ is

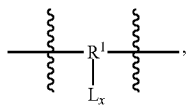

or $L^2$ is

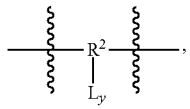

or
both $L^1$ is

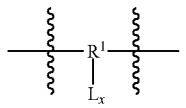

and $L^2$ is

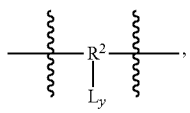

wherein each of $R^1$ and $R^2$ is independently selected from the group consisting of CR, NR, N and C(OR), wherein each R is independently H or an alkyl group (e.g., a $C_1$-$C_6$ alkyl); and each of $L_x$ and $L_y$ is independently a moiety selected from the group consisting of amide, ester, ether, thioether, hydrazone, urea, carbonate, thiol urea, carbamate, secondary amine bond, arylamine, amidine, phosporamidate, disulfide, sulfonamide, diazo, triazo bond formed through click chemistry.

P may be any suitable linear or branch oligomer of ethylene oxide.

Besides linear configurations, oligomers of ethylene oxide (or "PEGs") are also available with different geometries, for example, "branched" PEGs have three to ten PEG chains emanating from a central core group; "star" PEGs have 10 to 100 PEG chains emanating from a central core group; and "comb" PEGs have multiple PEG chains normally grafted onto a polymer backbone.

Examples of linear PEGs include:

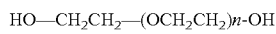

Examples of branched PEGs include:

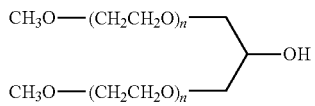

Examples of star PEGs include:

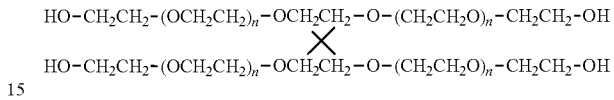

Examples of comb PEGs include:

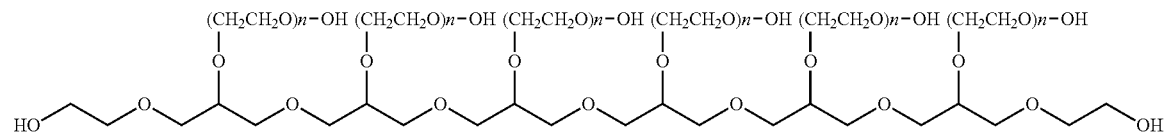

In certain embodiments, P is a branched PEG. In certain embodiments, P is a star PEG. In certain embodiments, P is a comb PEG.

m is an integer from 1 to about 10 (e.g., 1, 2, 3, 4, 5, 6, 7, 8, 9, 10), and n is an integer from 1 to about 10 (e.g., 1, 2, 3, 4, 5, 6, 7, 8, 9, 10). In certain embodiments, m=1 and n=1. In certain embodiments, m=1 and n is an integer selected from 2 to 7. In certain embodiments, n=1 and m is an integer selected from 2 to 7.

P may have any suitable number of ethylene oxide units. In certain embodiments, P is a linear or branched oligomer comprising from 1 to about 2,000 (e.g., from 1 to about 1,500, from 1 to about 1,200, from 1 to about 1,000, from 1 to about 800, from 1 to about 500, from 1 to about 200, from 1 to about 100, from 1 to about 50, from about 2 to about 2,000, from about 5 to about 2,000, from about 10 to about 2,000, from about 20 to about 2,000, from about 50 to about 2,000, from about 100 to about 2,000, from about 200 to about 2,000, from about 500 to about 2,000) ethylene oxide units.

In certain embodiments, P has a molecular weight from about 600 to about 50,000 (e.g., from about 600 to about 40,000, from about 600 to about 30,000, from about 600 to about 20,000, from about 600 to about 10,000, from about 600 to about 8,000, from about 600 to about 5,000, from about 600 to about 4,000, from about 600 to about 3,000, from about 600 to about 2,000, from about 1,000 to about 50,000, from about 2,000 to about 5,000, from about 10,000 to about 50,000, from about 20,000 to about 50,000, from about 30,000 to about 50,000, from about 1,000 to about 30,000, from about 1,000 to about 20,000, from about 1,000 to about 10,000).

$L^1$ and $L^2$ may be any suitable linking group or moiety and can be the same or different. At each occurrence, for example, $L^1$ and $L^2$ may independently comprises a moiety selected from the group consisting of amide, ester, ether, thioether, hydrazone, urea, carbonate, thiol urea, carbamate, secondary amine bond, arylamine, amidine, phosporamidate, disulfide, sulfonamide, diazo, triazo bond formed through click chemistry.

In certain preferred embodiments, $L^1$ and $L^2$, at each occurrence, independently comprises a moiety selected from the group consisting of amide, ester, ether, thioether, hydrazone, urea, carbonate, thiol urea, carbamate, secondary amine bond and disulfide.

Exemplary chemical linkers are showed in Table 3.

TABLE 3

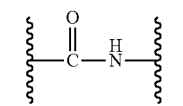

Amide linker

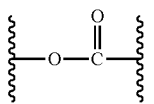

Ester linker

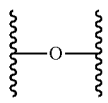

Ether linker

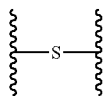

Thiol ether linker

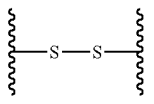 [SMILES: *SS*]

Disulfide linker

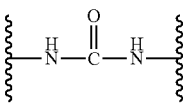 [SMILES: *NC(=O)N*]

Isourea linker

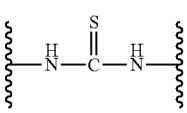 [SMILES: *NC(=S)N*]

Isothiourea linker

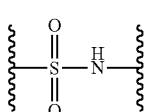

Sulfoamide linker

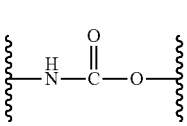

Carbamate linker

TABLE 3-continued

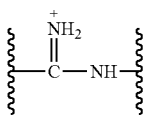

Amidine linker

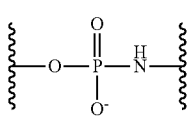

Phosphoramidate linker

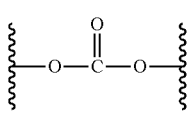 [SMILES: *OC(=O)O*]

Carbonate linker

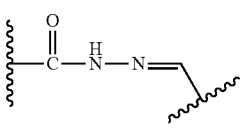 [SMILES: *C=NNC(*)=O]

Hydrazone linker

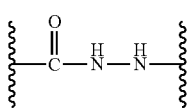 [SMILES: *NNC(*)=O]

Hydrazide linker

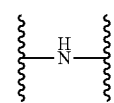

Second amine linker

Above linkers can be further modified, for example, with additional alkyl or other chemical bonds. Examples of some modified linkers are showed in Table 4.

TABLE 4

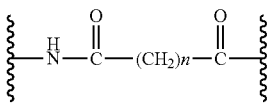

n = 1, 2, 3, 4, 5, 6

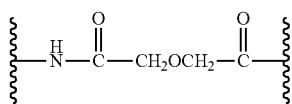

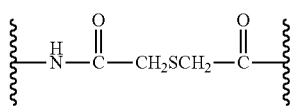

TABLE 4-continued

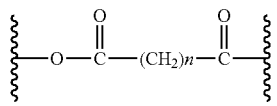

n = 1, 2, 3, 4, 5, 6

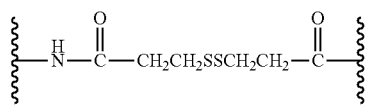

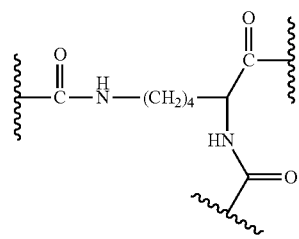

In certain preferred embodiments, one or both of $L^1$ and $L^2$ independently is a covalent linkage formed by click chemistry.

X may be any suitable fluorescently detectable moiety. In certain embodiments, X, at each occurrence, independently comprises a fluorescent dye, for example, selected from the group consisting of xanthene dyes, cyanine dyes, coumarin dyes, and bodipy dyes.

Dyes based on derivatives of xanthene are commonly referred to collectively as xanthene dyes. Among xanthene dyes are fluorescein, eosins, and rhodamines. Xanthene dyes tend to be fluorescent, yellow to pink to bluish red, brilliant dyes. Below are some examples of xanthene dyes.

TABLE 5

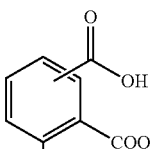

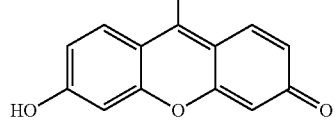

5(6)carboxyl fluorescein

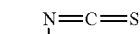

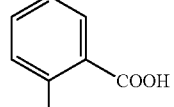

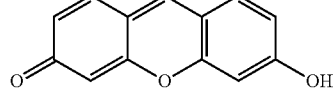

Fluorescein isothiocyanate

TABLE 5-continued

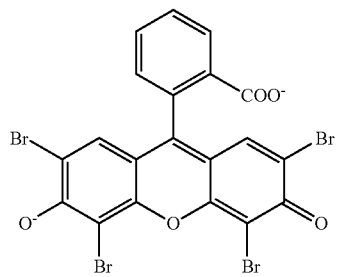

Eosin-Y

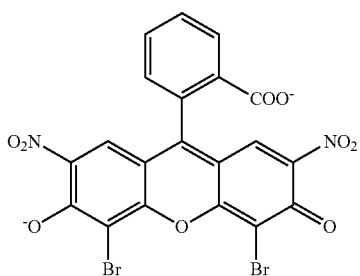

Eosin-B

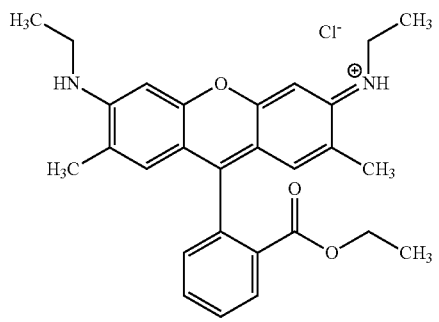 [SMILES: CCNc1cc2oc3c/c(=[NH+]\CC)c(C)cc-3c(-c3ccccc3C(=O)OCC)c2cc1C ; [Cl-]]

Rhodamine-6G

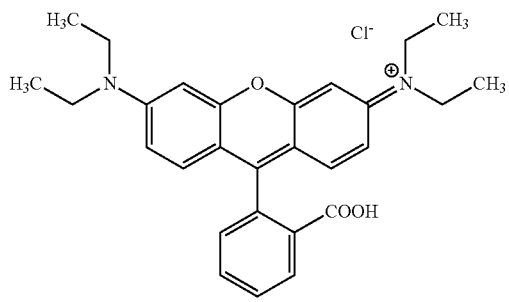 [SMILES: CCN(CC)c1ccc2c(-c3ccccc3C(=O)O)c3ccc(=[N+](CC)CC)cc-3oc2c1 ; [Cl-]]

Rhodamine-B

TABLE 5-continued
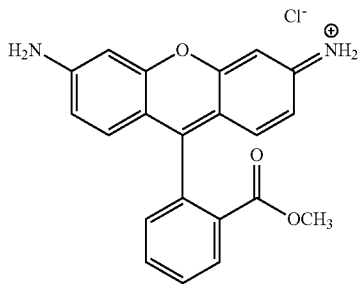 [SMILES: [Cl-] ; COC(=O)c1ccccc1-c1c2ccc(=[NH2+])cc-2oc2cc(N)ccc12]
Rhodamine 123
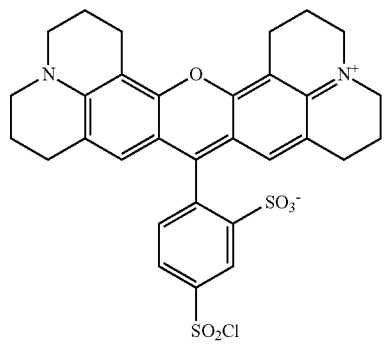
Sulforhodamine 101 acid chloride
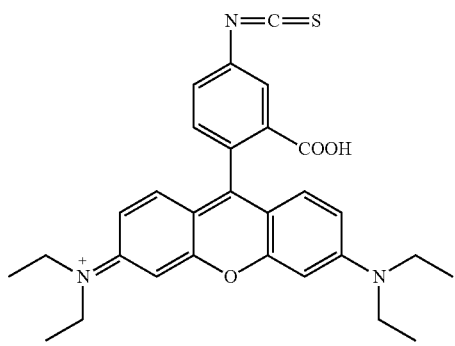
Rhodamine B isothiocyanate
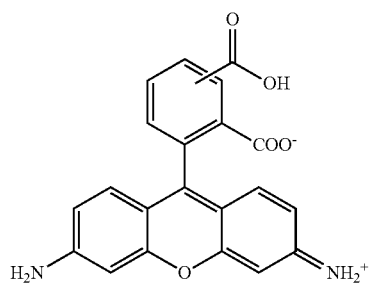
Rhodamine 110
TABLE 5-continued
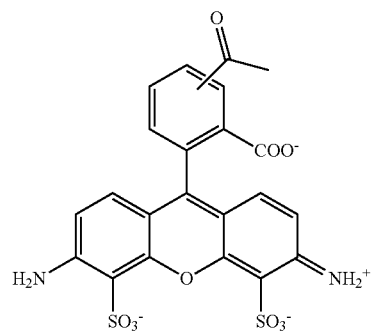
Alexa fluor 488
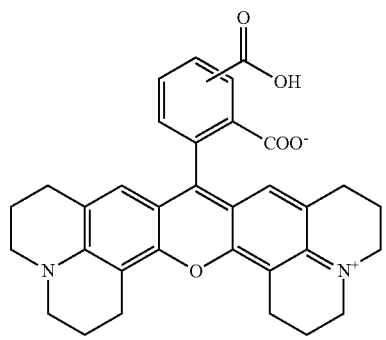
5(6)carboxyl-x-rhodamine
Other examples of xanthene dyes can be found in Table 6.
TABLE 6
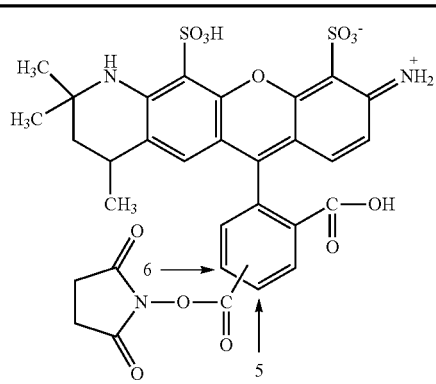
Alexa fluor 514

TABLE 6-continued

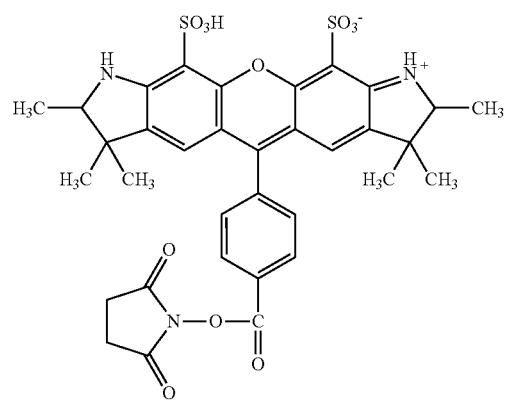

Alexa fluor 532

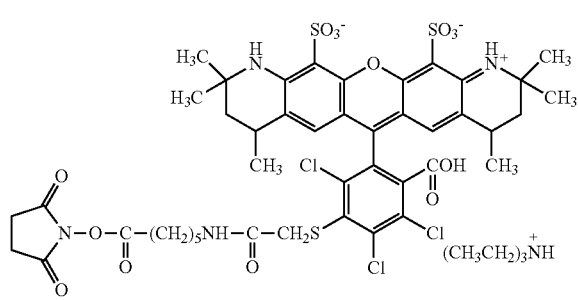

Alexa fluor 546

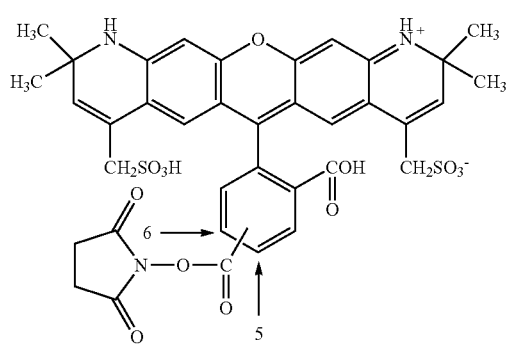

Alexa fluor 568

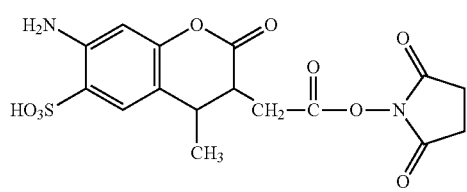 [SMILES: CC1c2cc(S(=O)(=O)O)c(N)cc2OC(=O)C1CC(=O)ON1C(=O)CCC1=O]

Alexa fluor 350

TABLE 6-continued

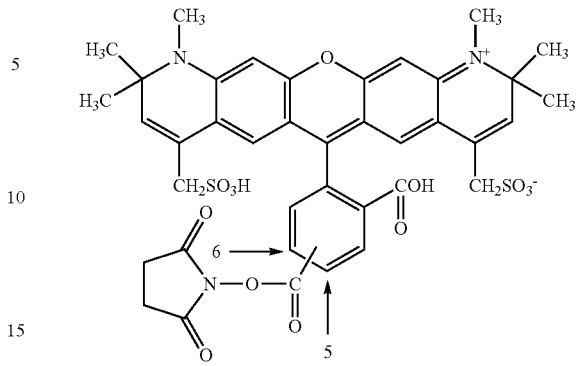

Alexa fluor 594

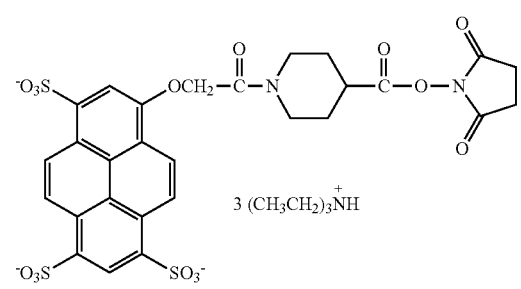

Alexa fluor 410

Cyanine dyes is a dye family of synthetic polymethine dyes (with the characteristic two nitrogens joined by a polymethine chain). Cyanine dyes can be categorized into three groups: streptocyanines, hemicyanines and closed cyanines, with general structures as follows.

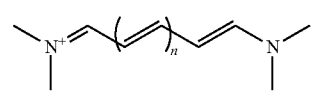

Streptocyanines

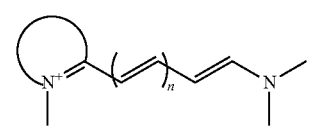

Hemicyanines

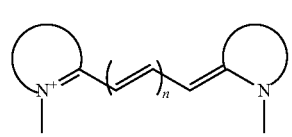

Closed cyanines

Below are some examples of cyanine dyes.
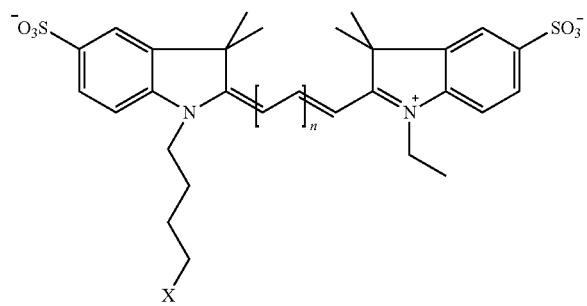
n = 1,2,3 for Cy3,5 or 7
X = ——COOH, ——NHS, maleimide, etc.
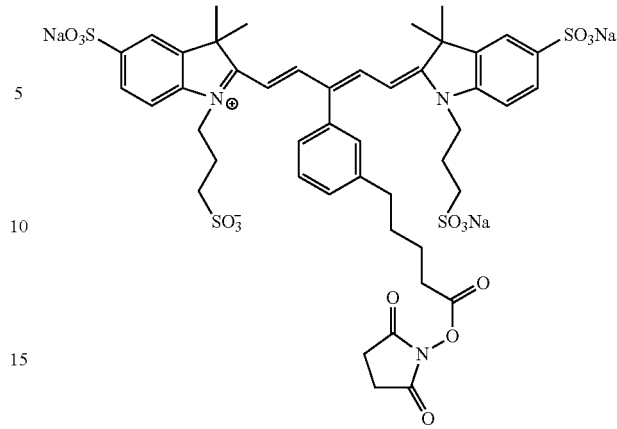
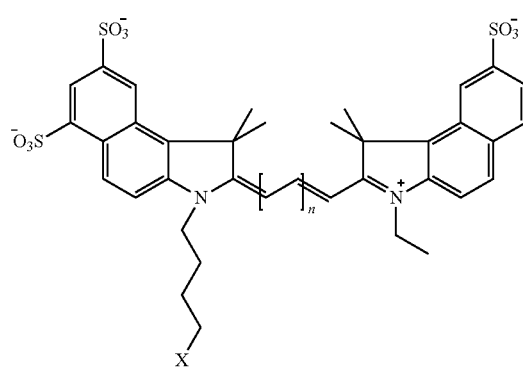
n = 1,2,3 for Cy3.5 ,5.5 or 7.5
X = ——COOH, ——NHS, maleimide, etc.
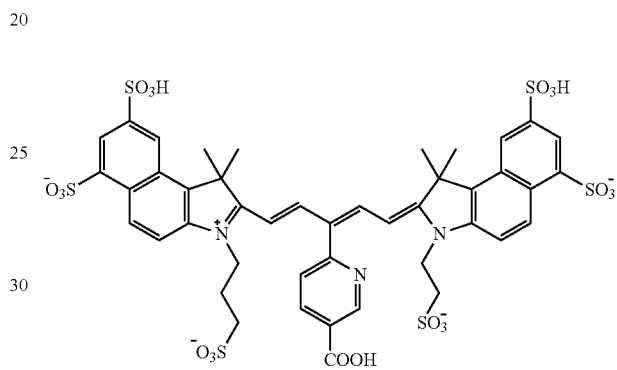
Other examples of cyanine dyes include the following compounds.
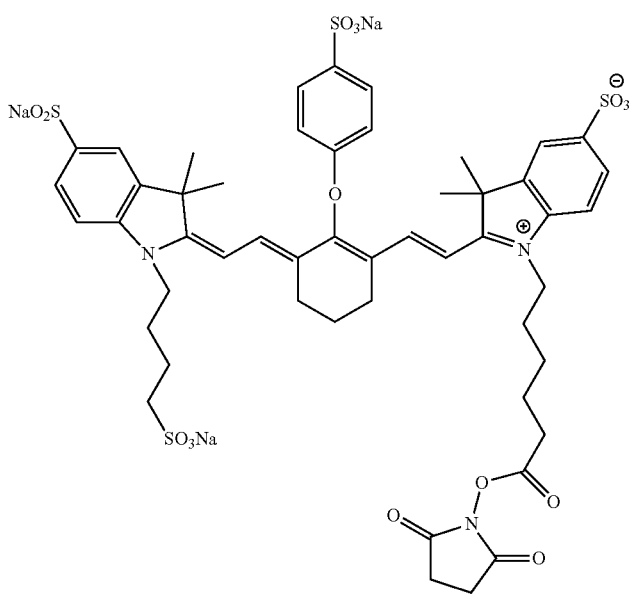
IRDye 800CW NHS

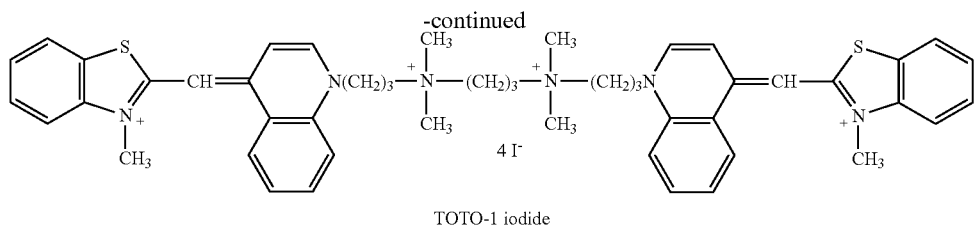

TOTO-1 iodide

Coumarin dyes refers to a class of dyes based on coumarin.

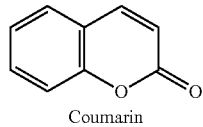

Coumarin

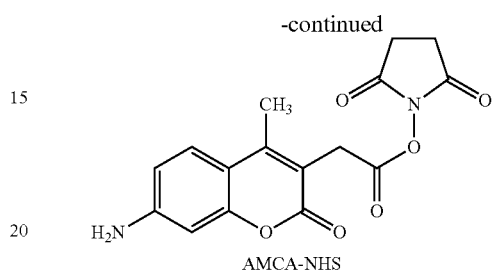

AMCA-NHS

Bodipy or boron-dipyrromethene dyes is a class of fluorescent dyes characterized by a dipyrromethene complexed with a disubstituted boron atom, typically a $BF_2$ unit.

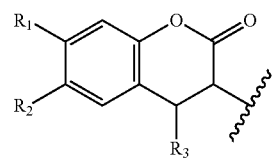

General structure of coumarin dyes

Below are some examples of coumarin dyes.

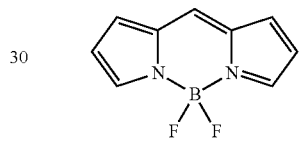

Bodipy

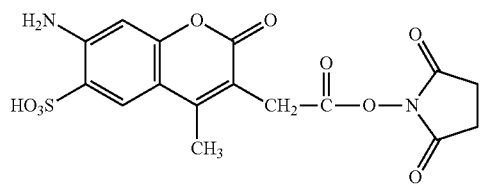

Alexa Fluor 350

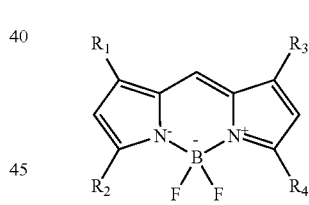

General Structure of bodipy dyes

Examples of bodipy dyes include:

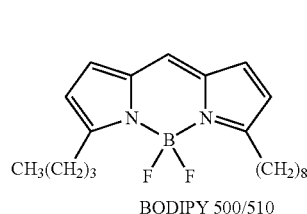

BODIPY 500/510

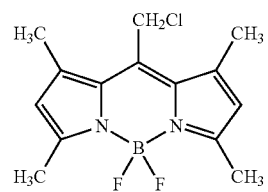

Cell tracker BODIPY Green

-continued

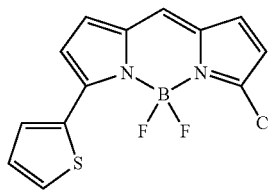

BODIPY 630/650-X, SE

Y may be any suitable chemically reactive moiety or biologically active moiety.

In certain embodiments, each Y is independently a chemically reactive moiety selected from the group consisting of amino, carboxyl, hydroxyl, thiol, vinyl, vinyl sulfone, tosyl, succinimidyl ester, aldehyde, isocyanate, isothiocyante, epoxy, maleimide, silanes. azide, hydrazide, alkyne, cycloalkynes, aminoxy, nitrophenyl, thiol pyridyl, halogen, and halogen acetate.

Examples of conjugate compounds with Y's that are chemically reactive are listed in Table 7.

TABLE 7

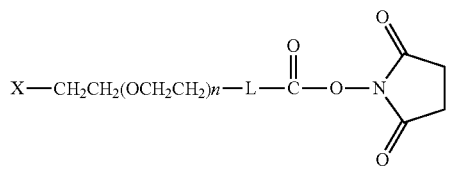

Succinimidyl ester PEG, L is a linker

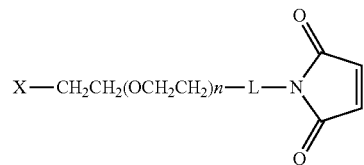

Maleimide PEG, L is a linker

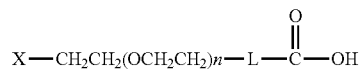

X—CH$_2$CH$_2$(OCH$_2$CH$_2$)$n$—L—NH$_2$

X—CH$_2$CH$_2$(OCH$_2$CH$_2$)$n$—L—SH

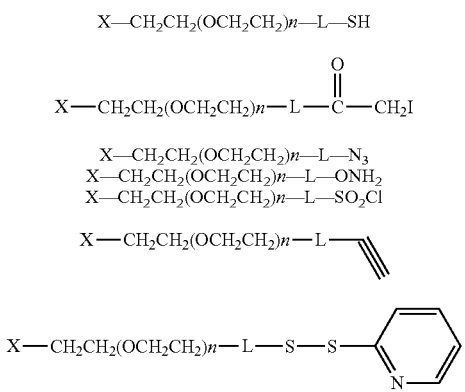

X—CH$_2$CH$_2$(OCH$_2$CH$_2$)$n$—L—N$_3$
X—CH$_2$CH$_2$(OCH$_2$CH$_2$)$n$—L—ONH$_2$
X—CH$_2$CH$_2$(OCH$_2$CH$_2$)$n$—L—SO$_2$Cl

TABLE 7-continued

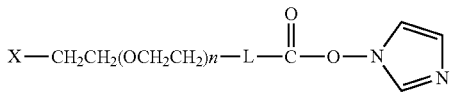

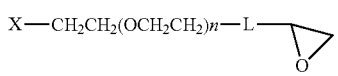

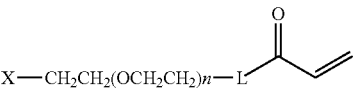

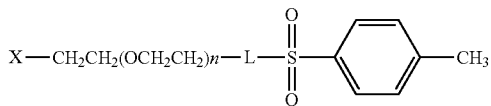

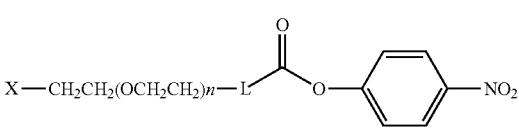

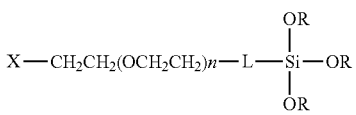

In certain embodiments, each Y is independently a biologically active moiety selected from the group consisting of enzyme inhibitors, vitamins, lipids, phospholipids, cholesterol, peptides, nucleotides, carbohydrates, and receptor binding ligands.

Examples of conjugate compounds with Y's that are biologically active are listed in Table 8.

TABLE 8
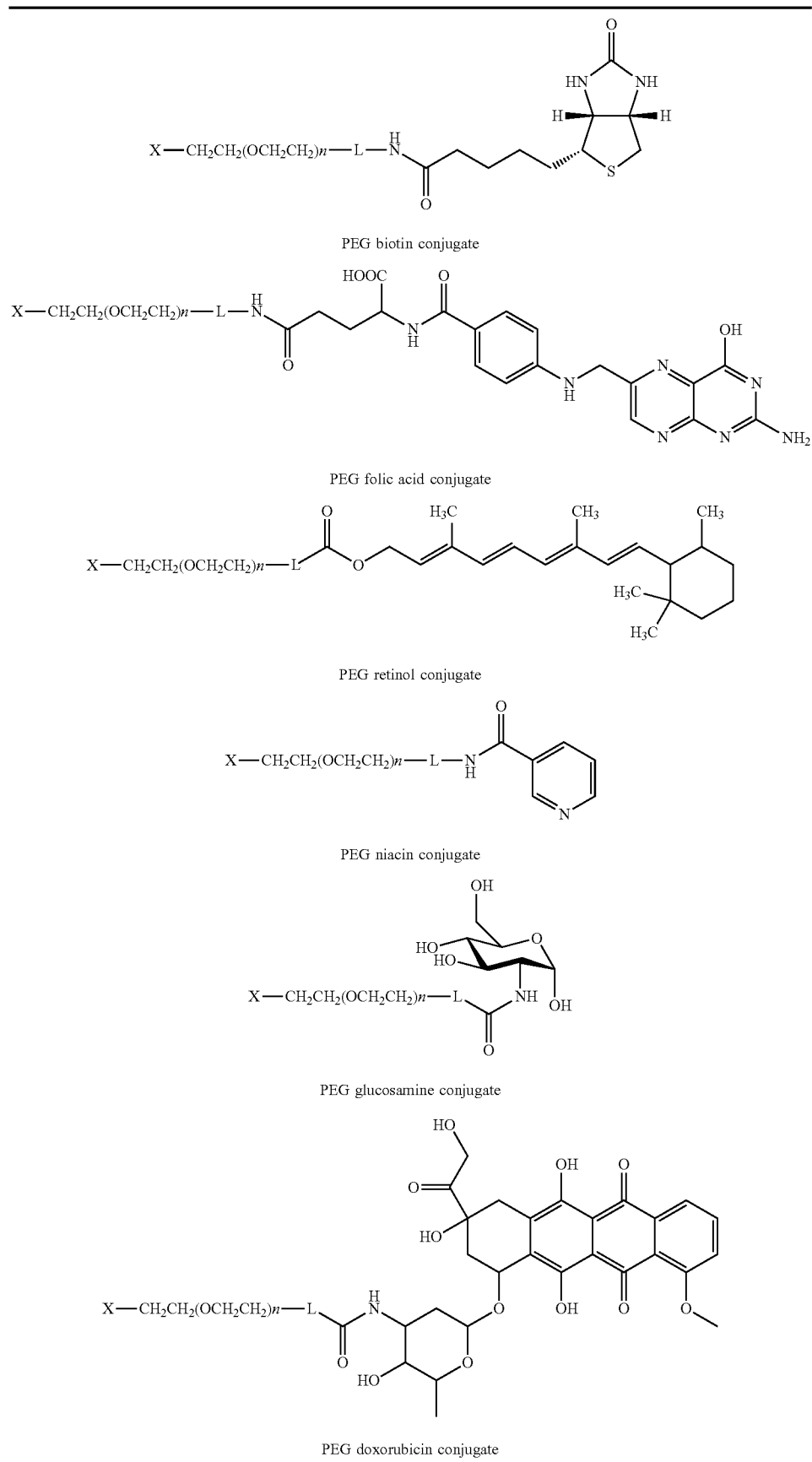

TABLE 8-continued
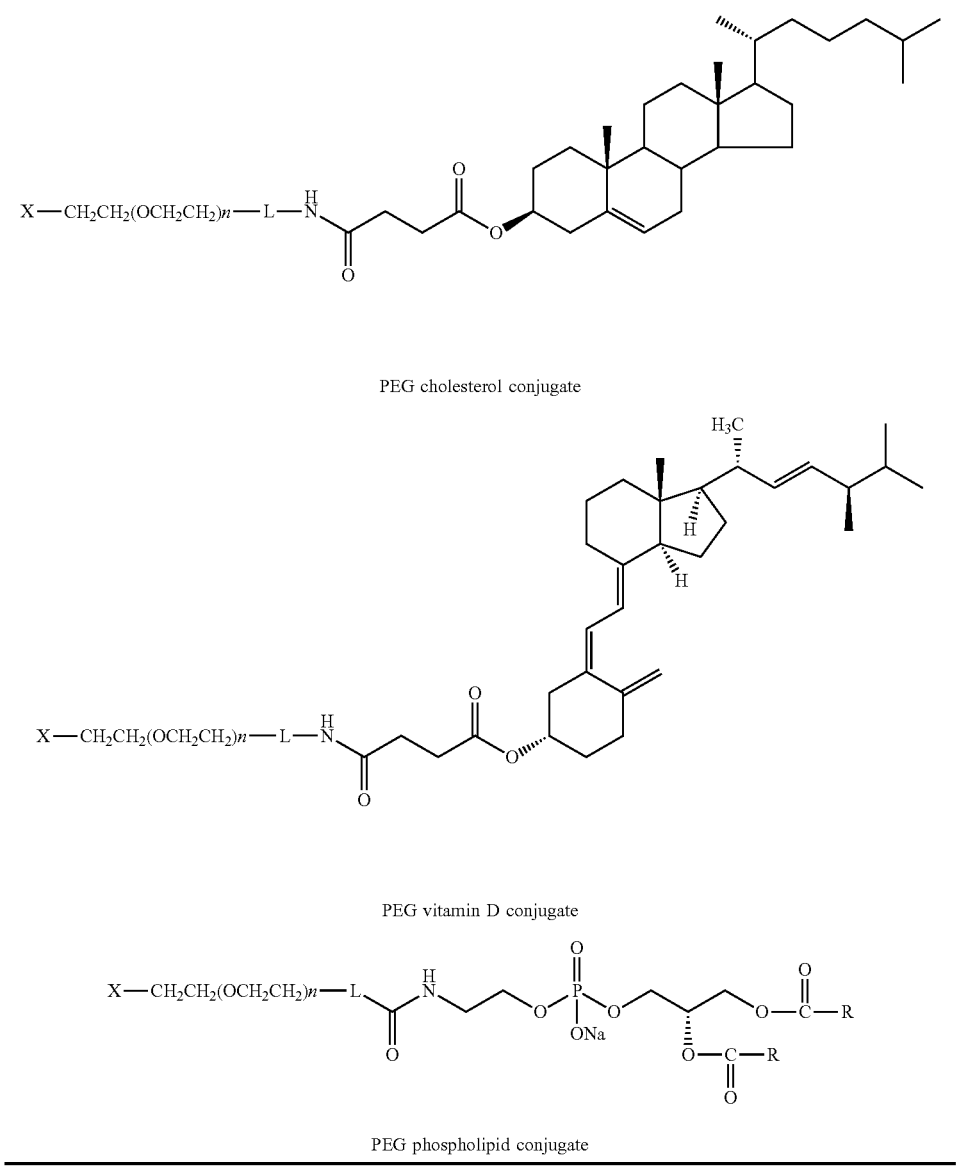
PEG cholesterol conjugate
PEG vitamin D conjugate
PEG phospholipid conjugate
Exemplary conjugate compounds of the invention are listed in Table 9.
TABLE 9
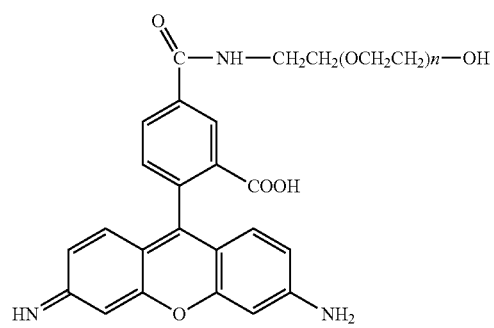
1

TABLE 9-continued
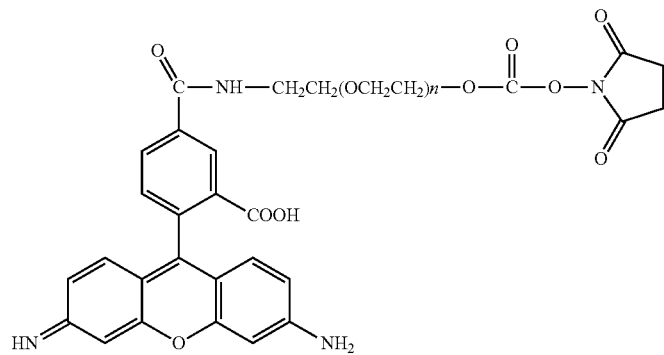
2
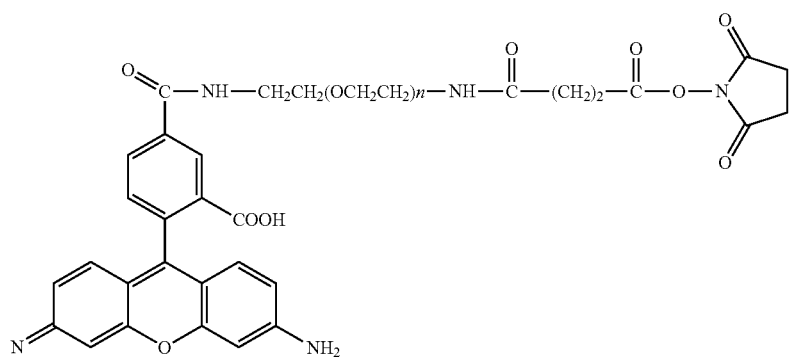
3
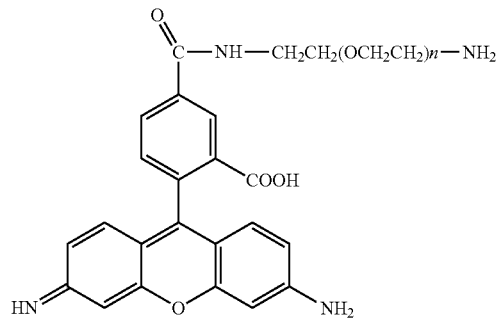
4
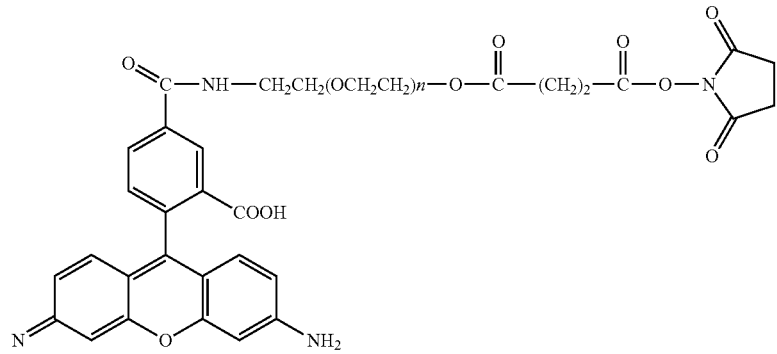
5

TABLE 9-continued
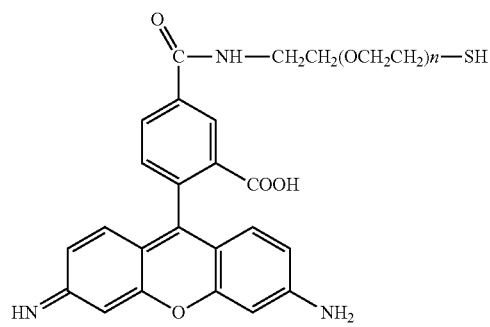 6
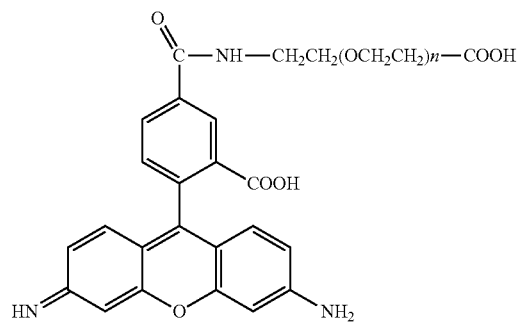 7
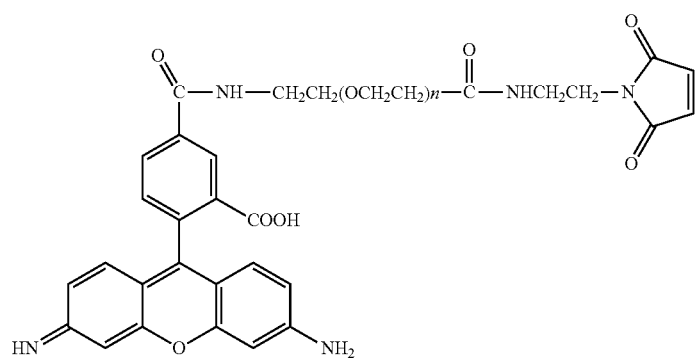 8
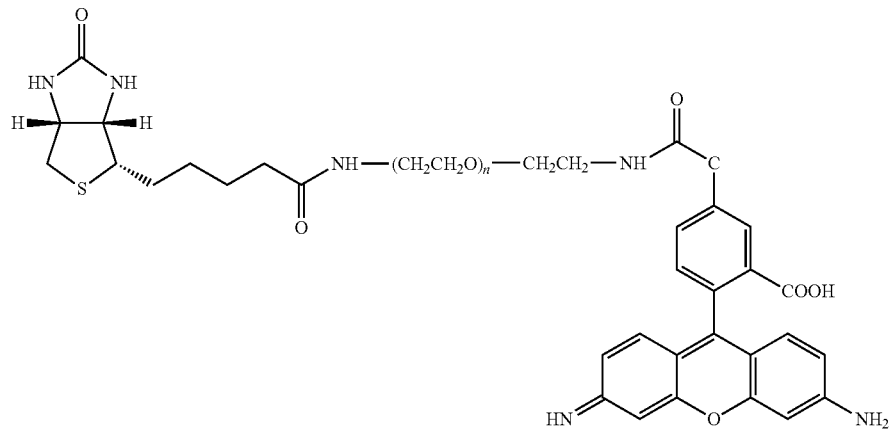 9

TABLE 9-continued
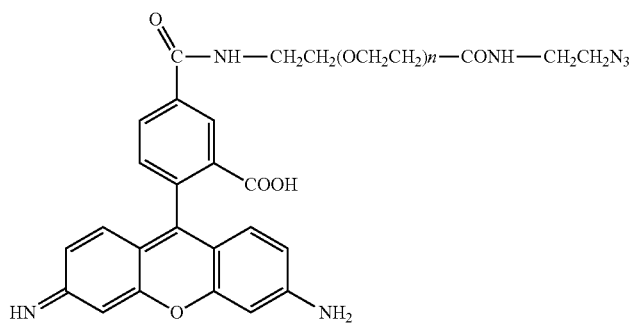
10
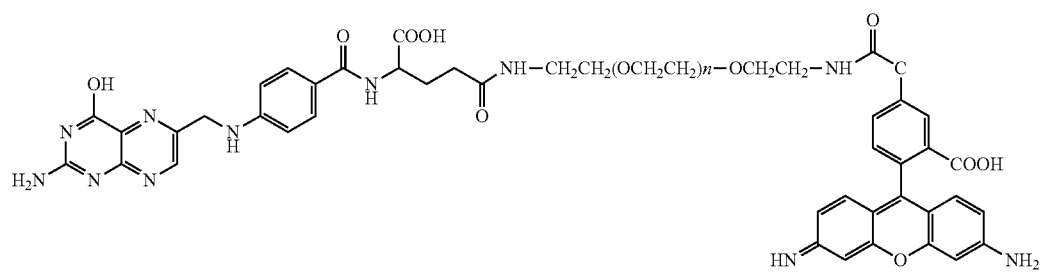
11
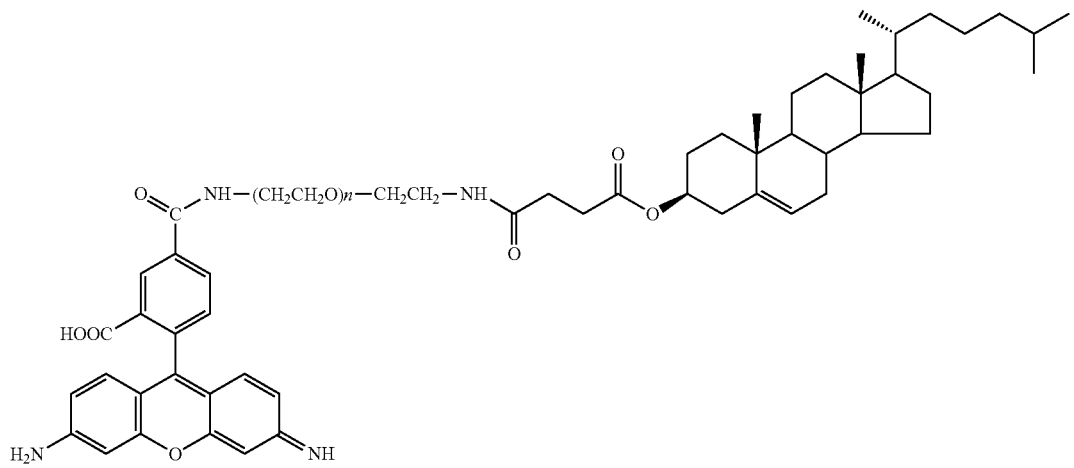
12
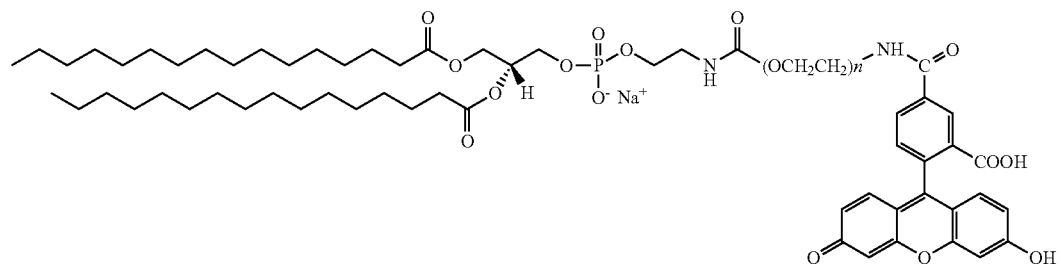
13

TABLE 9-continued
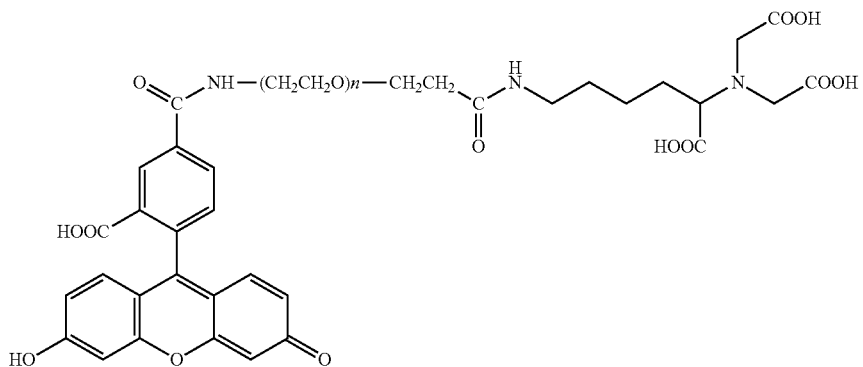
14
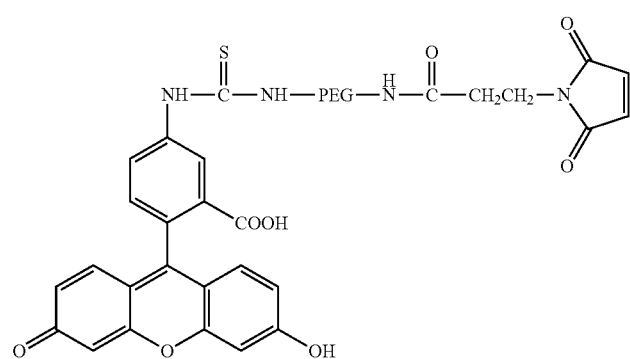
15
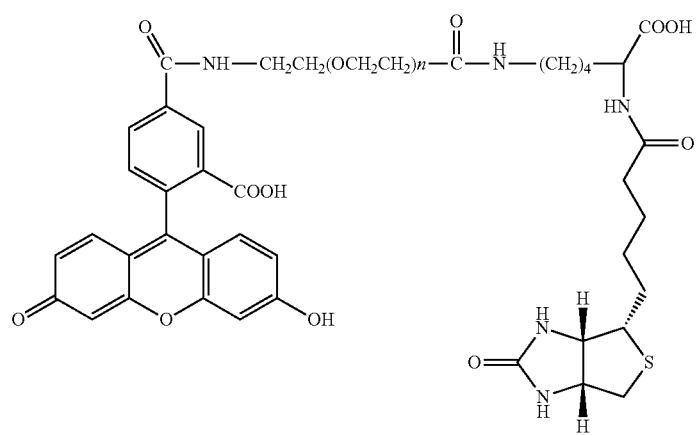
16
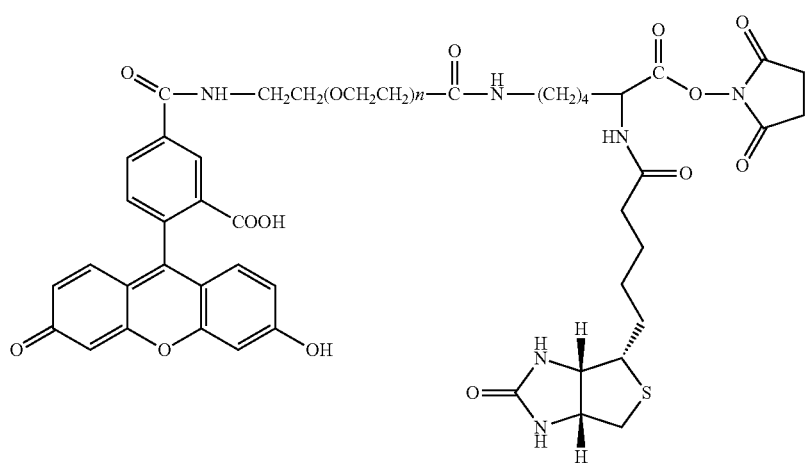
17

TABLE 9-continued
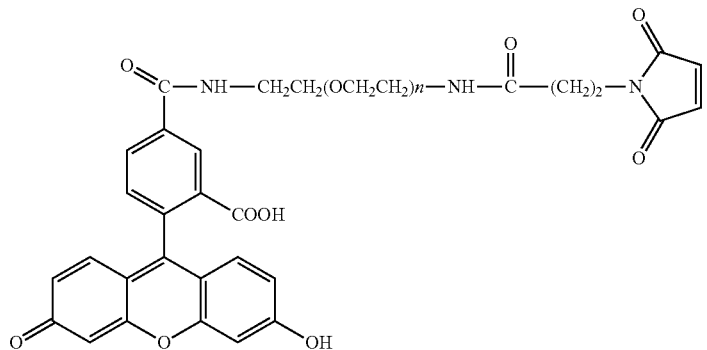
18
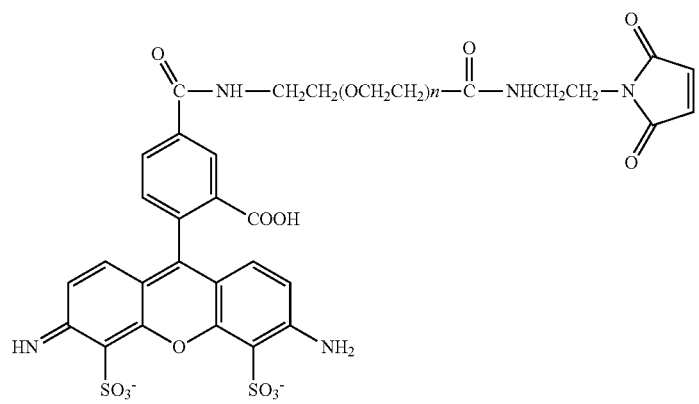
19
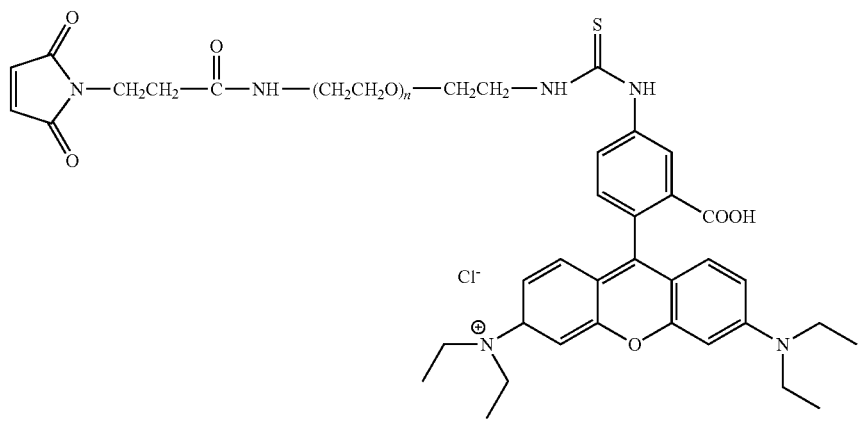
20
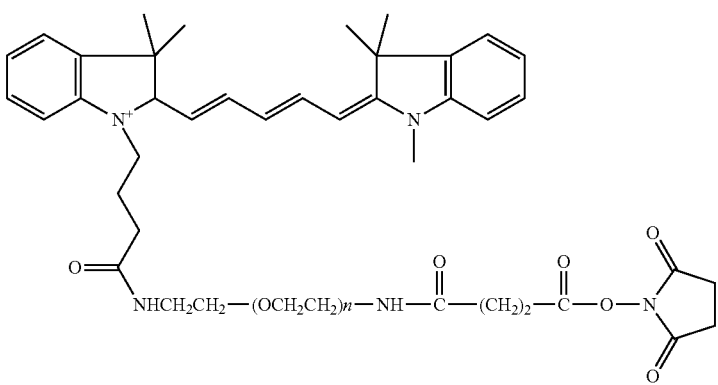
21

TABLE 9-continued
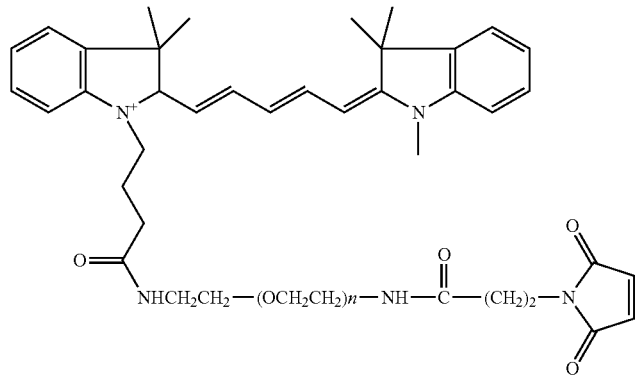
22
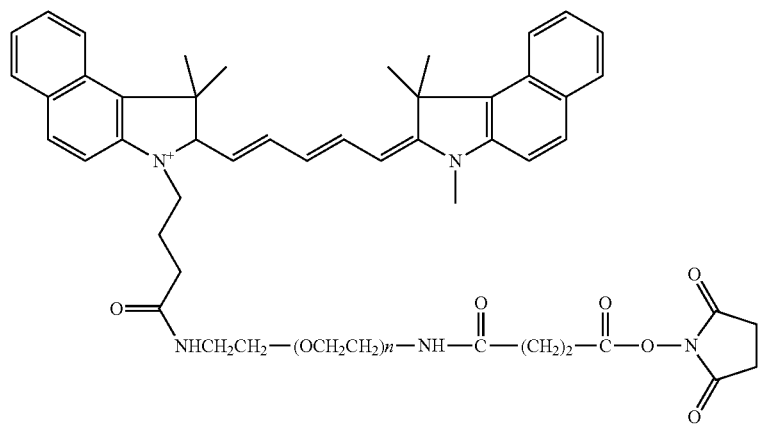
23
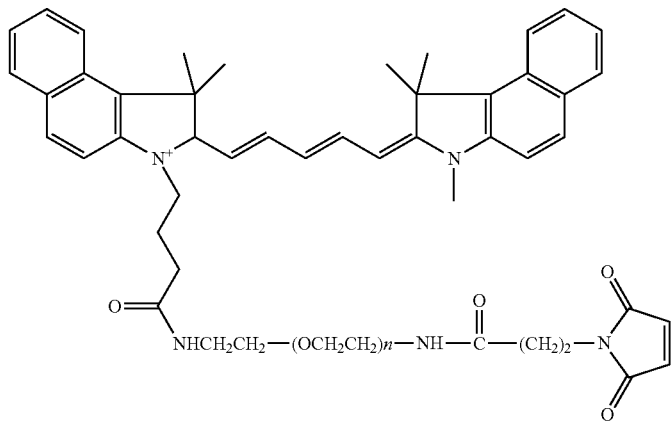
24
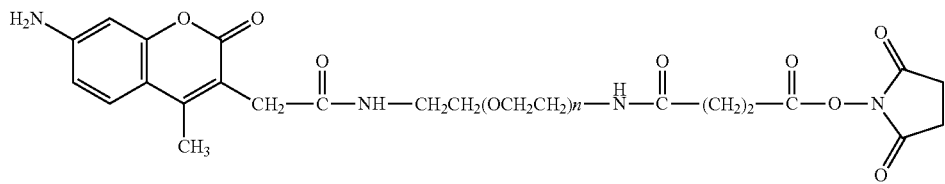
25

TABLE 9-continued

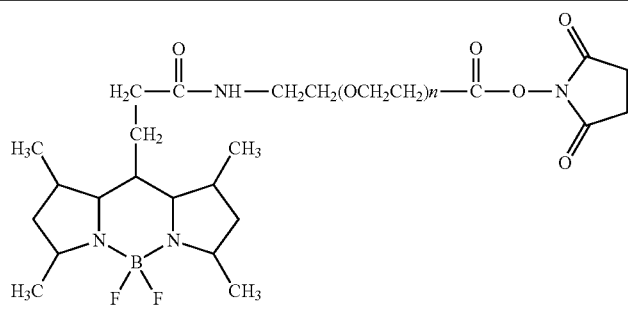

26

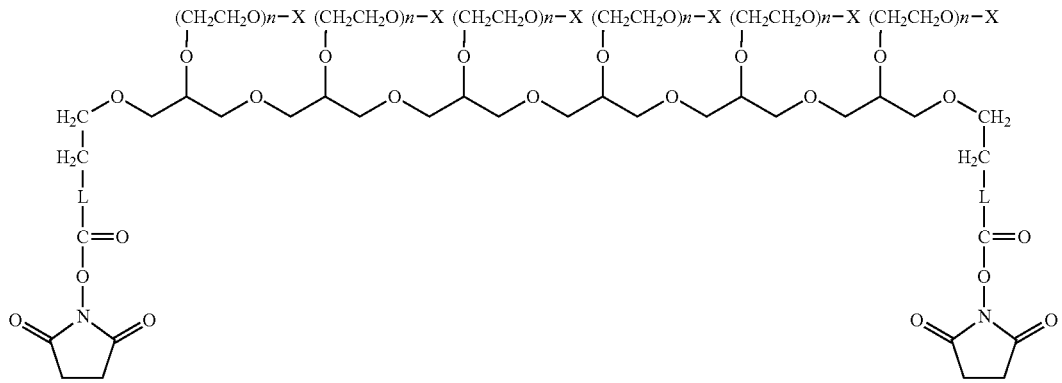

27

X may be dyes, biotins, and/or other functional groups

In another aspect, the invention generally relates to a method of labeling a target with a fluorescently detectable moiety. The method includes: contacting a conjugate compound disclosed herein with the target under a condition such that a covalent or non-covalent conjugate is formed between the compound and the target.

In certain embodiments, the target is a cell. In certain embodiments, the target is selected from an antibody, a protein or a nucleic acid.

EXAMPLES

Example 1

Synthesis of Compound 1

$NH_2$-PEG-OH, MW 3400 (34 mg, 0.01 mmol) from Nanocs was dissolved in 10 mL dichloromethane at room temperature, to this solution, Rhodamine 110 succinimidyl NHS (0.12 mmol, 6.10 mg) was added, followed by the addition of 5 drops of $Et_3N$. The mixture was stirred at room temperature for 12 hours. The organic solvent was evaporated and the mixture was recrystalized with ethyl acetate and diethyl ether for 3 times. A brick red solid material was obtained. To obtain more pure compound, this material was redissolved in de-ionized water and pure compound was separated by HPLC.

Example 2

Synthesis of Compound 2

Compound 1 (20 mg) synthesized from example 1 was dissolved in dry DMF, to this solution, DSC (N,N'-Disuccinimidyl carbonate) (10.2 mg, 0.04 mmol) was added, followed by the addition of 0.5 mL $Et_3N$. Above mixture was stirred at room temperature for 12 hours. Ice cold diethyl ether was added to the above reaction solution and brick red solid was collected by filtration. Obtained solid was re-dissolved in warm toluene, undissolved solid was filtered off, Organic solvent in solution was evaporated under reduced pressure. Cold diethyl ethyl was added to the residue solution and resulting brick red solid was collected by filtration. More pure compound can be obtained by HPLC purification.

Example 3

Synthesis of Compound 3

34 mg PEG compound with amino and carboxylic groups, linked by an amide bond ($NH_2$—$CH_2CH_2(OCH_2CH_2)$n-NHCO$(CH_2)_2$—COOH, MW 3400 was obtained from Fisher Scientific. This compound was dissolved in 10 mL methylene chloride, subsequently, Rhodamine 110 succinimidyl NHS (0.12 mmol, 6.10 mg) was added, followed by the addition of 5 drops of $Et_3N$. The mixture was stirred at room temperature for 12 hours. The organic solvent was evaporated and the mixture was recrystalized with ethyl acetate and diethyl ether. 17 mg Obtained solid was dissolved in 10 mL methylene chloride, DCC (dicyclohexyl carbodiimide) (21 mg) and NHS (N-hydroxy succinimide) (10 mg) was added subsequently. Above mixture was stirred at temperature for overnight. White precipitate was filtered and solvent was evaporated under reduced pressure. Cold diethyl ethyl was added to the residue solution and resulting brick red solid was collected by filtration.

Example 4

Synthesis of Compound 4

0.1 g Fmoc-NH-PEG-NH$_2$, MW 5000, purchased from Fisher Scientific, was dissolved in 10 mL acetonitrile (CH$_3$CN) in a 50 mL glass flask, under vigorous stirring, 20 mg Rhodamine 110 succinimidyl ester was added slowly. After addition of rhodamine 110 NHS, 0.01 mL triethyl amine (Et3N) was added to above solution as catalyst. Reaction was allowed to proceed for 12 hours protected under argon and light. Reaction was stopped and most solvent was evaporated under reduced pressure. Resulting solution was added with cold diethyl ether and brick red solid was filtered and washed 3 times with cold diethyl ether. To deprotect Fmoc group, above obtained compound was dissolved in 10 mL DMF, 2 mL piperidine was added to the above solution and reaction allows for 2 hours. Solvent was evaporated under reduced pressure and wash with cold diethyl ether for 3 times. Compound 4 was further purified with chromatograph and dried under vacuum.

Example 5

Synthesis of Compound 5

Procedures are similar to Example 3 except using PEG compound with amino and carboxylic groups, linked by an ester bond (NH$_2$—CH$_2$CH$_2$(OCH$_2$CH$_2$)n-COO(CH$_2$)$_2$—COOH.

Example 6

Synthesis of Compound 7

Procedures are similar to Example 1 except using carboxyl PEG amine, NH$_2$—CH$_2$CH$_2$(OCH$_2$CH$_2$)n-COOH, MW 3400 as starting material.

Example 7

Synthesis of Compound 8

Rhodamine 110 PEG amine, compound 4 (8 mg) was dissolved in 10 mL methylene chloride, to this solution, Maleimide propionic succinimidyl ester (1.5 mg) was added, 2 drops of Et$_3$N was added to the solution as catalyst. Reaction proceeded for overnight at room temperature. Organic solvent was evaporated under reduced pressure. Cold ethyl ether was added to the residue solution and resulting brick red solid was collected by filtration.

Example 8

Synthesis of Compound 9

Rhodamine 110 PEG amine, compound 4 (8 mg) was dissolved in 10 mL methylene chloride, to this solution, Biotin-NHS (1.5 mg) was added, 2 drops of Et$_3$N was added to the solution as catalyst. Reaction was stirred with magnetic stirrer for overnight at room temperature. Organic solvent was evaporated under reduced pressure. Cold ethyl ether was added to the residue solution and resulting brick red solid was collected by filtration.

Example 9

Synthesis of Compound 11

Folic acid NHS (10 mg) was dissolved in 10 mL DMSO, to this solution, 34 mg rhodamine 110 PEG amine, MW 3400 was added slowly. Above mixture was added with 10 drops of triethyl amine as catalyst. Solution was stirred with magnetic stirrer for overnight at room temperature. Organic solvent was concentrated under reduced pressure. 30/70 acetone/ethyl ether was added to the residue solution and resulting brick red solid was collected by filtration.

Example 9

Synthesis of Compound 16

34 mg 5(6)fluorescein PEG NHS, MW 3400 synthesized with the similar procedures as described in example 5, was dissolved in 10 mL dry DMSO, to this solution, 3 mg lysine was added slowly. Afterwards, 5 drops of Et3N was added as catalyst. Reaction mixture was protected with argon and was stirred for 12 hours at room temperature. Organic solvent was concentrated under reduced pressure. Cold ethyl ether was added to the residue solution and resulting yellow/orange solid was collected by filtration. Crude solid was further purified with HPLC. This compound is designated as Fluorescein PEG Lys. To obtain compound 16, 17 mg Fluorescein PEG Lys was dissolved in 5 mL methylene chloride, to this solution, 2 mg Biotin NHS was added, a drop of Et3N was added subsequently as catalyst. Mixture was stirred for 12 hour at room temperature, protected from argon. Reaction was stopped and solvent was concentrated under reduced pressure. Cold ethyl ether was added to the residue solution and yellow solid was collected by filtration. More pure compound was obtained by HPLC purification.

Example 10

Synthesis of Compound 27

100 mg (0.005 mmol) 8 branched amino PEG, MW 20000, was dissolved in 10 mL methylene chloride, to this solution, 14.16 mg (0.03 mmol) 5(6)-carboxyfluorescein succinimidyl NHS was added. 5 mg Triethyl amine was added subsequently as catalyst. Reaction mixture was protected with aluminum foil and stirred at room temperature. Reaction was stopped after 12 hours and solvent was evaporated under reduced pressure. Cold ethyl ether was added into solvent residue and resulting yellow/orange solid was collected by filtration. Crude compound was purified with HPLC. Compound with six fluoresceins was collected and dried in vacuum. Above collected compound (20 mg) was redissolved in methylene chloride and disuccinimidyl succinate (2 mg) was added, together with 5 drops of triethyl amine. Mixture was stirred for 12 hours and organic solvent was evaporated under reduced pressure. Cold ether was added into residue solvent and yellow/orange solid was collected by filtration. Compound was further purified by HPLC to obtain final compound 27.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A compound having a structural formula selected from the group consisting of:

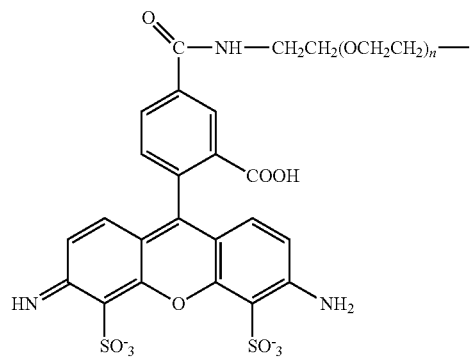

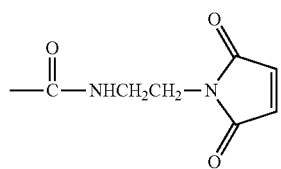

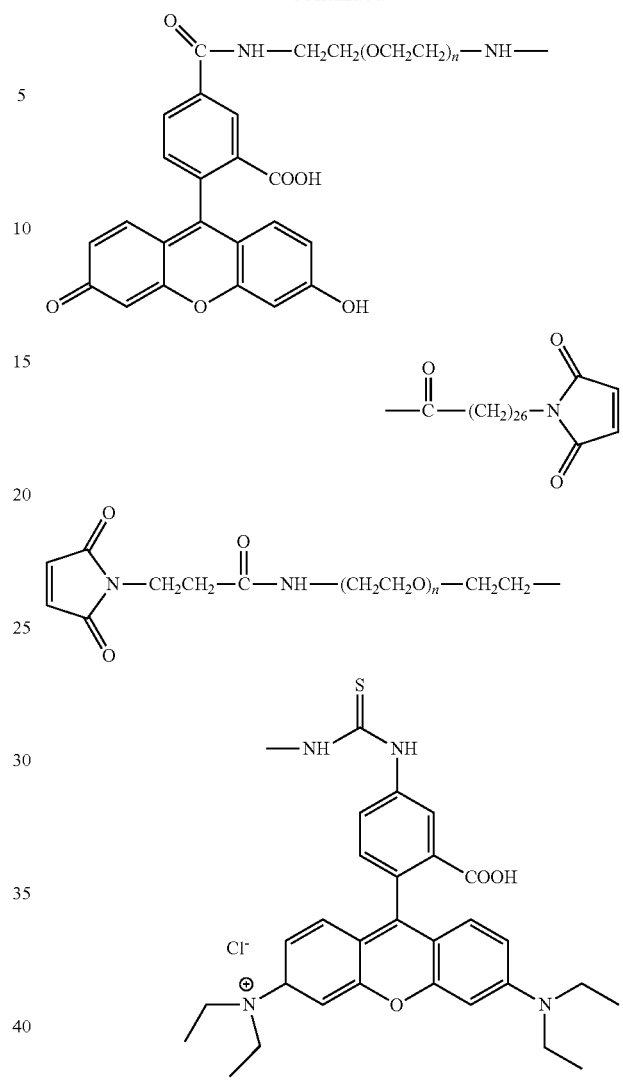

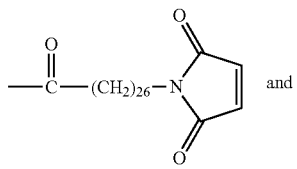

-continued
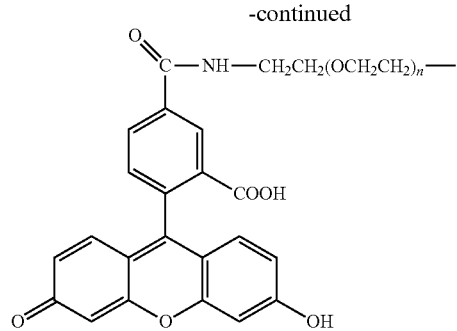
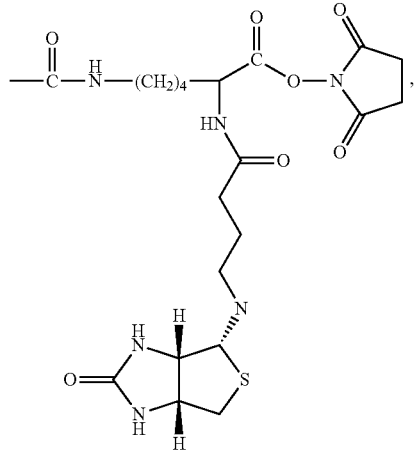
wherein n is 1 to about 2000.
2. The compound of claim 1, wherein the compound is:
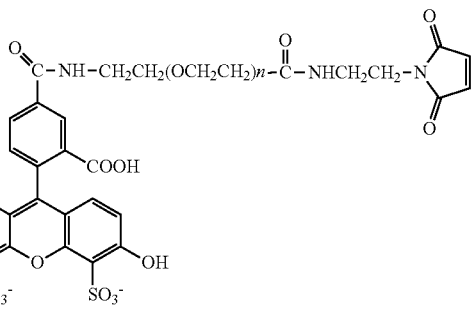
3. The compound of claim 1, wherein the compound is:
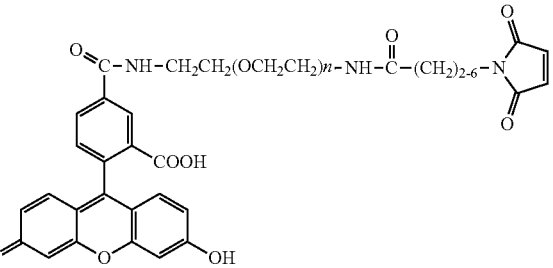
4. The compound of claim 1, wherein the compound is:
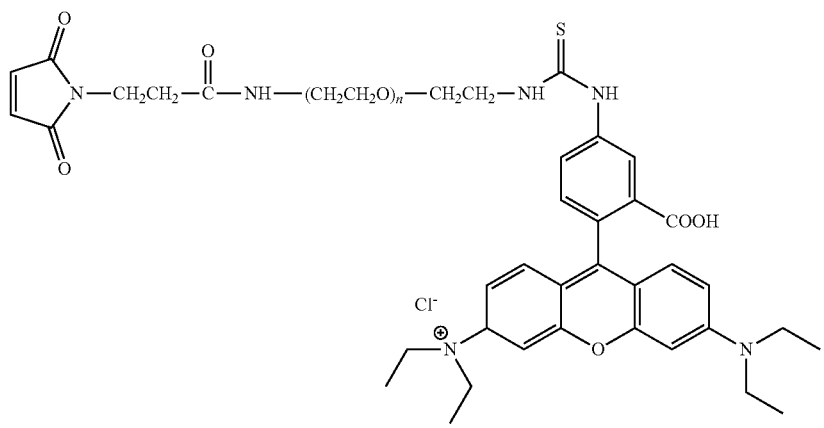

5. The compound of claim 1, wherein the compound is:
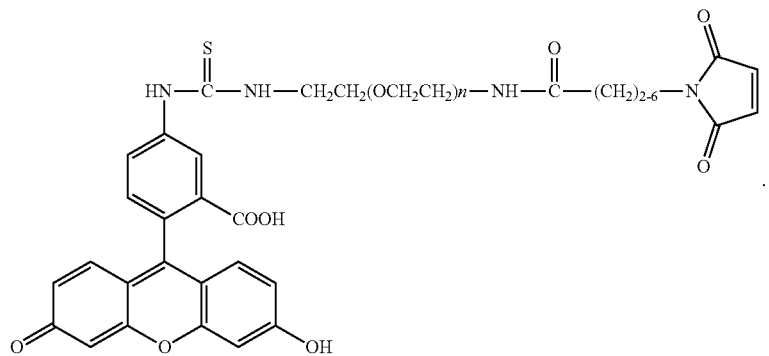
6. The compound of claim 1, wherein the compound is
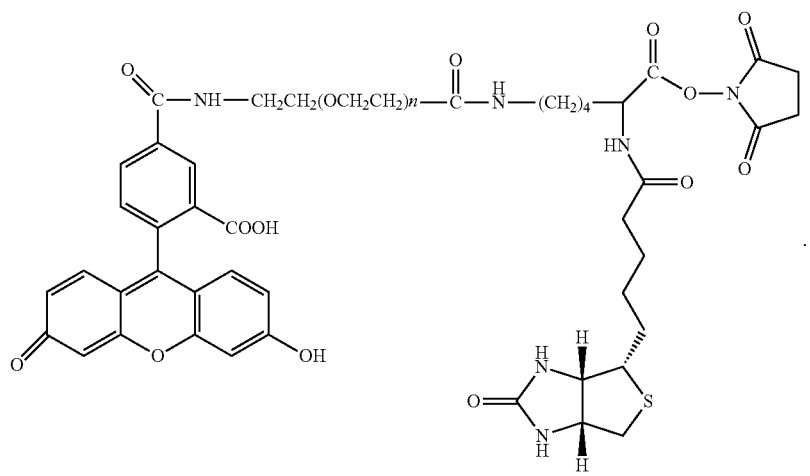
* * * * *